United States Patent
Zhang et al.

(10) Patent No.: US 7,772,456 B2
(45) Date of Patent: Aug. 10, 2010

(54) STRETCHABLE ABSORBENT COMPOSITE WITH LOW SUPERABORBENT SHAKE-OUT

(75) Inventors: Xiaomin Zhang, Appleton, WI (US);
David Martin Jackson, Alpharetta, GA (US); Lisa Marie Jacobsen, Roswell, GA (US); Jian Qin, Appleton, WI (US); Dave Allen Soerens, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 501 days.

(21) Appl. No.: 10/883,174

(22) Filed: Jun. 30, 2004

(65) Prior Publication Data

US 2006/0004336 A1    Jan. 5, 2006

(51) Int. Cl.
*A61F 13/15* (2006.01)
*A61F 13/20* (2006.01)
*C08L 83/00* (2006.01)
*C09D 151/00* (2006.01)

(52) U.S. Cl. .................. 604/368; 604/367; 523/201

(58) Field of Classification Search ......... 604/367–368, 604/358, 385.01; 428/295.1, 296.1, 299.7, 428/294.7; 502/402, 526; 252/184; 523/201
See application file for complete search history.

(56) References Cited

U.S. PATENT DOCUMENTS

| | | | |
|---|---|---|---|
| 3,338,992 A | 8/1967 | Kinney | |
| 3,339,546 A | 9/1967 | Chen | |
| 3,341,394 A | 9/1967 | Kinney | |
| 3,485,706 A | 12/1969 | Evans | |
| 3,502,538 A | 3/1970 | Petersen | |
| 3,502,763 A | 3/1970 | Hartmann | |

(Continued)

FOREIGN PATENT DOCUMENTS

DE    296 14 542 U1    2/1997

(Continued)

OTHER PUBLICATIONS

Graph from "Normal Distribution"; partial citation from Wikipedia entry; full entry annotated with citations and bibliography, http://en.wikipedia.org/wiki/Normal_distribution.*

(Continued)

*Primary Examiner*—Melanie J Hand
(74) *Attorney, Agent, or Firm*—Paul Y. Yee; David J. Arteman; Bryan R. Rosiejka

(57) ABSTRACT

An article comprises a stretchable absorbent composite (30) that includes a quantity of superabsorbent particles (32) which are operatively contained within a matrix of elastomeric polymer fibers (34). In particular aspects, the composite article can include at least about 60 wt % of the superabsorbent particles and not more than about 40 wt % of the elastomeric polymer fibers, based on a total weight of the composite. In other aspects, the composite article can provide a high stretchability. Additional aspects can provide a low shake-out. Particular configurations can, for example, provide a stretchability value of at least about 30%. Additional aspects can include a configuration that provides a shake-out value of not more than about 2%. In further aspects, the absorbent composite can include superabsorbent particles having a coating of treatment-material that is thermally processible. Additional aspects can include a treatment-material which is water soluble.

19 Claims, 4 Drawing Sheets

U.S. PATENT DOCUMENTS

| | | |
|---|---|---|
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,855,046 A | 12/1974 | Hansen et al. |
| 3,901,236 A * | 8/1975 | Assarsson et al. ............ 604/368 |
| 3,966,865 A | 6/1976 | Nishida et al. |
| 4,055,180 A | 10/1977 | Karami |
| 4,076,663 A | 2/1978 | Masuda et al. |
| 4,100,324 A | 7/1978 | Anderson et al. |
| 4,286,082 A | 8/1981 | Tsubakimoto et al. |
| 4,327,728 A | 5/1982 | Elias |
| 4,340,563 A | 7/1982 | Appel et al. |
| 4,360,021 A | 11/1982 | Stima |
| 4,369,156 A | 1/1983 | Mathes et al. |
| 4,392,908 A * | 7/1983 | Dehnel ....................... 427/194 |
| 4,427,737 A | 1/1984 | Cilento et al. |
| 4,429,001 A | 1/1984 | Kolpin et al. |
| 4,469,734 A | 9/1984 | Minto et al. |
| 4,488,928 A | 12/1984 | Ali Khan et al. |
| 4,530,353 A | 7/1985 | Lauritzen |
| 4,542,199 A | 9/1985 | Kaminsky et al. |
| 4,547,420 A | 10/1985 | Krueger et al. |
| 4,551,191 A | 11/1985 | Kock et al. |
| 4,587,154 A | 5/1986 | Hotchkiss et al. |
| 4,588,630 A | 5/1986 | Shimalla |
| 4,604,313 A | 8/1986 | McFarland et al. |
| 4,610,678 A | 9/1986 | Weisman et al. |
| 4,654,038 A | 3/1987 | Sakurai |
| 4,655,757 A | 4/1987 | McFarland et al. |
| 4,704,116 A | 11/1987 | Enloe |
| 4,715,918 A | 12/1987 | Lang |
| 4,724,114 A | 2/1988 | McFarland et al. |
| 4,729,371 A | 3/1988 | Krueger et al. |
| 4,767,825 A | 8/1988 | Pazos et al. |
| 4,775,579 A | 10/1988 | Hagy et al. |
| 4,795,668 A | 1/1989 | Krueger et al. |
| 4,803,117 A | 2/1989 | Daponte |
| 4,806,408 A | 2/1989 | Pierre et al. |
| 4,818,464 A | 4/1989 | Lau |
| 4,834,738 A | 5/1989 | Kielpikowski et al. |
| RE32,957 E | 6/1989 | Elias |
| 4,838,885 A | 6/1989 | Bernardin |
| 4,865,596 A | 9/1989 | Weisman et al. |
| 4,879,170 A | 11/1989 | Radwanski et al. |
| 4,880,419 A | 11/1989 | Ness |
| 4,891,258 A | 1/1990 | Fahrenkrug |
| 4,904,440 A | 2/1990 | Angstadt |
| 4,923,914 A | 5/1990 | Nohr et al. |
| 4,935,022 A | 6/1990 | Lash et al. |
| 4,939,016 A | 7/1990 | Radwanski et al. |
| 4,940,464 A | 7/1990 | Van Gompel et al. |
| 4,957,795 A | 9/1990 | Riedel |
| 4,960,477 A | 10/1990 | Mesek |
| 4,988,344 A | 1/1991 | Reising et al. |
| 4,996,091 A | 2/1991 | McIntyre |
| 5,057,166 A | 10/1991 | Young, Sr. et al. |
| 5,064,689 A | 11/1991 | Young, Sr. et al. |
| 5,064,802 A | 11/1991 | Stevens et al. |
| 5,108,820 A | 4/1992 | Kaneko et al. |
| 5,114,781 A | 5/1992 | Morman |
| 5,116,662 A | 5/1992 | Morman |
| 5,143,680 A | 9/1992 | Molnar et al. |
| 5,149,335 A | 9/1992 | Kellenberger et al. |
| 5,154,715 A | 10/1992 | Van Iten |
| 5,169,706 A | 12/1992 | Collier, IV et al. |
| 5,171,391 A | 12/1992 | Chmielewski et al. |
| 5,188,624 A | 2/1993 | Young, Sr. et al. |
| 5,189,192 A | 2/1993 | Lapointe et al. |
| 5,204,429 A | 4/1993 | Kaminsky et al. |
| 5,213,881 A | 5/1993 | Timmons et al. |
| 5,221,275 A | 6/1993 | Van Iten |
| 5,225,014 A | 7/1993 | Ogata et al. |
| 5,230,959 A | 7/1993 | Young, Sr. et al. |
| 5,248,524 A | 9/1993 | Soderlund |
| 5,260,126 A | 11/1993 | Collier, IV et al. |
| 5,272,236 A | 12/1993 | Lai et al. |
| 5,273,596 A | 12/1993 | Newkirk |
| 5,278,272 A | 1/1994 | Lai et al. |
| 5,279,854 A | 1/1994 | Kendall et al. |
| 5,281,207 A | 1/1994 | Chmielewski et al. |
| 5,281,209 A | 1/1994 | Osborn, III et al. |
| 5,284,703 A | 2/1994 | Everhart et al. |
| 5,288,791 A | 2/1994 | Collier, IV et al. |
| 5,290,626 A | 3/1994 | Nishioi et al. |
| 5,302,447 A | 4/1994 | Ogata et al. |
| 5,308,906 A | 5/1994 | Taylor et al. |
| 5,332,613 A | 7/1994 | Taylor et al. |
| 5,336,552 A | 8/1994 | Strack et al. |
| 5,344,416 A | 9/1994 | Niihara et al. |
| 5,349,100 A | 9/1994 | Mintz |
| 5,350,597 A | 9/1994 | Pelley |
| 5,350,624 A | 9/1994 | Georger et al. |
| 5,352,749 A | 10/1994 | Dechellis et al. |
| 5,354,400 A | 10/1994 | Lavash et al. |
| 5,364,382 A * | 11/1994 | Latimer et al. ............... 604/378 |
| 5,366,793 A | 11/1994 | Fitts, Jr. et al. |
| 5,372,885 A | 12/1994 | Tabor et al. |
| 5,374,696 A | 12/1994 | Rosen et al. |
| 5,376,198 A | 12/1994 | Fahrenkrug et al. |
| 5,382,400 A | 1/1995 | Pike et al. |
| 5,385,775 A * | 1/1995 | Wright ....................... 442/183 |
| 5,387,208 A | 2/1995 | Ashton et al. |
| 5,389,094 A | 2/1995 | Lavash et al. |
| 5,389,202 A | 2/1995 | Everhart et al. |
| 5,411,497 A | 5/1995 | Tanzer et al. |
| 5,421,940 A | 6/1995 | Cornils et al. |
| 5,424,115 A | 6/1995 | Stokes |
| 5,425,725 A | 6/1995 | Tanzer et al. |
| 5,432,000 A | 7/1995 | Young, Sr. et al. |
| 5,433,715 A | 7/1995 | Tanzer et al. |
| 5,458,592 A | 10/1995 | Abuto et al. |
| 5,486,166 A | 1/1996 | Bishop et al. |
| 5,490,846 A | 2/1996 | Ellis et al. |
| 5,503,908 A | 4/1996 | Faass |
| 5,508,102 A | 4/1996 | Georger et al. |
| 5,509,914 A | 4/1996 | Osborn, III |
| 5,509,915 A | 4/1996 | Hanson et al. |
| 5,511,960 A | 4/1996 | Terakawa et al. |
| 5,516,585 A | 5/1996 | Young, Sr. et al. |
| 5,518,801 A | 5/1996 | Chappell et al. |
| 5,520,673 A | 5/1996 | Yarbrough et al. |
| 5,527,300 A | 6/1996 | Sauer |
| 5,560,878 A | 10/1996 | Dragoo et al. |
| 5,562,645 A | 10/1996 | Tanzer et al. |
| 5,562,646 A | 10/1996 | Goldman et al. |
| 5,567,472 A | 10/1996 | Siegfried et al. |
| 5,591,147 A | 1/1997 | Couture Dorschner et al. |
| 5,591,149 A | 1/1997 | Cree et al. |
| 5,593,399 A | 1/1997 | Tanzer et al. |
| 5,599,335 A | 2/1997 | Goldman et al. |
| 5,601,542 A | 2/1997 | Melius et al. |
| 5,611,790 A | 3/1997 | Osborn, III et al. |
| 5,614,283 A | 3/1997 | Potnis et al. |
| 5,620,430 A | 4/1997 | Bamber |
| 5,643,245 A | 7/1997 | Osborn, III et al. |
| 5,645,542 A | 7/1997 | Anjur et al. |
| 5,669,894 A | 9/1997 | Goldman et al. |
| 5,670,044 A | 9/1997 | Ogata et al. |
| 5,676,660 A | 10/1997 | Mukaida et al. |
| 5,679,042 A | 10/1997 | Varona |
| 5,681,305 A | 10/1997 | Korpman |
| 5,683,752 A | 11/1997 | Popp et al. |
| 5,691,035 A | 11/1997 | Chappell et al. |

| Patent No. | Date | Inventor |
|---|---|---|
| 5,704,930 A | 1/1998 | Lavash et al. |
| 5,713,881 A | 2/1998 | Rezai et al. |
| 5,713,884 A | 2/1998 | Osborn, III et al. |
| 5,713,885 A | 2/1998 | Jorgenson et al. |
| 5,718,913 A | 2/1998 | Dhuique-Mayer et al. |
| 5,720,832 A | 2/1998 | Minto et al. |
| 5,759,926 A | 6/1998 | Pike et al. |
| 5,766,389 A | 6/1998 | Brandon et al. |
| 5,772,648 A | 6/1998 | Osborn, III et al. |
| 5,789,065 A | 8/1998 | Haffner et al. |
| 5,820,973 A | 10/1998 | Dodge, II et al. |
| 5,824,004 A | 10/1998 | Osborn, III et al. |
| 5,833,678 A | 11/1998 | Ashton et al. |
| 5,843,059 A | 12/1998 | Niemeyer et al. |
| 5,849,000 A | 12/1998 | Anjur et al. |
| 5,853,881 A | 12/1998 | Estey et al. |
| 5,858,292 A | 1/1999 | Dragoo et al. |
| 5,858,515 A | 1/1999 | Stokes et al. |
| 5,879,751 A | 3/1999 | Bogdanski |
| 5,882,769 A | 3/1999 | McCormack et al. |
| 5,883,028 A | 3/1999 | Morman et al. |
| 5,891,120 A | 4/1999 | Chmielewski |
| 5,900,109 A | 5/1999 | Sanders et al. |
| 5,904,675 A | 5/1999 | Laux et al. |
| 5,922,163 A | 7/1999 | Helynranta et al. |
| 5,938,650 A | 8/1999 | Baer et al. |
| 5,964,743 A | 10/1999 | Abuto et al. |
| 5,977,014 A | 11/1999 | Plischke et al. |
| 5,981,410 A | 11/1999 | Hansen et al. |
| 5,981,689 A | 11/1999 | Mitchell et al. |
| 5,994,440 A | 11/1999 | Staples et al. |
| 6,013,062 A | 1/2000 | Dilnik |
| 6,046,377 A | 4/2000 | Huntoon et al. |
| 6,060,115 A | 5/2000 | Borowski et al. |
| 6,068,620 A | 5/2000 | Chmielewski |
| 6,072,101 A | 6/2000 | Beihoffer et al. |
| 6,080,909 A | 6/2000 | Osterdahl et al. |
| 6,087,448 A | 7/2000 | Mitchell et al. |
| 6,090,875 A | 7/2000 | Staples et al. |
| 6,102,902 A | 8/2000 | Jackson |
| 6,121,409 A | 9/2000 | Mitchell et al. |
| 6,129,720 A | 10/2000 | Blenke et al. |
| 6,159,591 A | 12/2000 | Beihoffer et al. |
| 6,194,631 B1 | 2/2001 | Mitchell et al. |
| 6,200,297 B1 | 3/2001 | Boulanger |
| 6,214,274 B1 | 4/2001 | Melius et al. |
| 6,221,062 B1 | 4/2001 | Osborn, III |
| 6,222,091 B1 | 4/2001 | Beihoffer et al. |
| 6,231,557 B1 | 5/2001 | Krautkramer et al. |
| 6,235,965 B1 | 5/2001 | Beihoffer et al. |
| 6,241,713 B1 | 6/2001 | Gross et al. |
| 6,248,202 B1 | 6/2001 | Corzani et al. |
| 6,261,679 B1 | 7/2001 | Chen et al. |
| 6,264,784 B1 | 7/2001 | Menard et al. |
| 6,277,105 B1 | 8/2001 | Rynish |
| 6,280,428 B1 | 8/2001 | Lash et al. |
| 6,287,288 B1 | 9/2001 | Osborn, III et al. |
| 6,290,686 B1 | 9/2001 | Tanzer |
| 6,309,378 B1 | 10/2001 | Costa |
| 6,312,416 B1 | 11/2001 | Brisebois et al. |
| 6,328,722 B1 | 12/2001 | Lavash et al. |
| 6,342,298 B1 | 1/2002 | Evans et al. |
| 6,353,148 B1 | 3/2002 | Gross |
| 6,362,389 B1 * | 3/2002 | McDowall et al. .......... 604/367 |
| 6,363,389 B1 | 3/2002 | Lyle et al. |
| 6,371,950 B1 | 4/2002 | Roslansky et al. |
| 6,372,952 B1 | 4/2002 | Lash et al. |
| 6,376,072 B1 | 4/2002 | Evans et al. |
| 6,387,084 B1 | 5/2002 | VanGompel et al. |
| 6,387,495 B1 | 5/2002 | Reeves et al. |
| 6,392,116 B1 | 5/2002 | Beihoffer et al. |
| 6,403,857 B1 | 6/2002 | Gross et al. |
| 6,416,502 B1 | 7/2002 | Connelly et al. |
| 6,428,523 B1 | 8/2002 | Proglhof |
| 6,429,350 B1 | 8/2002 | Tanzer et al. |
| 6,440,113 B1 | 8/2002 | Brisebois et al. |
| 6,441,266 B1 | 8/2002 | Dyer et al. |
| 6,455,114 B1 | 9/2002 | Goldhirsch et al. |
| 6,455,753 B1 | 9/2002 | Glaug et al. |
| 6,465,712 B1 * | 10/2002 | Matthews et al. ........... 604/378 |
| 6,468,942 B1 | 10/2002 | Sansalone |
| 6,470,943 B1 | 10/2002 | Borowski et al. |
| 6,494,871 B1 | 12/2002 | Lariviere et al. |
| 6,500,159 B1 | 12/2002 | Carvalho |
| 6,503,234 B1 | 1/2003 | Canuel et al. |
| 6,509,512 B1 | 1/2003 | Beihoffer et al. |
| 6,509,513 B2 | 1/2003 | Glaug et al. |
| 6,515,195 B1 | 2/2003 | Lariviere et al. |
| 6,527,757 B1 | 3/2003 | Jackson |
| 6,534,572 B1 * | 3/2003 | Ahmed et al. ................ 524/275 |
| 6,552,245 B1 | 4/2003 | Roessler et al. |
| 6,555,502 B1 | 4/2003 | Beihoffer et al. |
| 6,562,742 B2 | 5/2003 | Dutkiewicz et al. |
| 6,570,058 B1 | 5/2003 | Fuchs et al. |
| 6,579,274 B1 | 6/2003 | Morman et al. |
| 6,582,413 B2 | 6/2003 | Krautkramer et al. |
| 6,590,138 B2 | 7/2003 | Onishi |
| 6,603,054 B2 | 8/2003 | Chen et al. |
| 6,605,552 B2 | 8/2003 | Jackson et al. |
| 6,610,900 B1 | 8/2003 | Tanzer |
| 6,627,564 B1 | 9/2003 | Morman et al. |
| 6,632,209 B1 | 10/2003 | Chmielewski |
| 6,641,134 B1 | 11/2003 | Dobbertin et al. |
| 6,641,695 B2 | 11/2003 | Baker |
| 6,645,190 B1 | 11/2003 | Olson et al. |
| 6,646,179 B1 | 11/2003 | Melius et al. |
| 6,646,180 B1 | 11/2003 | Chmielewski |
| 6,680,423 B1 * | 1/2004 | Tanzer ........................ 604/380 |
| 2001/0001312 A1 | 5/2001 | Mitchell et al. |
| 2001/0007064 A1 | 7/2001 | Mitchell et al. |
| 2001/0029358 A1 | 10/2001 | Beihoffer et al. |
| 2001/0044612 A1 | 11/2001 | Beihoffer et al. |
| 2002/0007166 A1 | 1/2002 | Mitchell et al. |
| 2002/0015846 A1 | 2/2002 | Evans et al. |
| 2002/0077618 A1 | 6/2002 | Molas |
| 2002/0095127 A1 | 7/2002 | Fish et al. |
| 2002/0150761 A1 | 10/2002 | Lange et al. |
| 2002/0156441 A1 | 10/2002 | Sawyer et al. |
| 2002/0183703 A1 | 12/2002 | Singh et al. |
| 2003/0014027 A1 | 1/2003 | Beihoffer et al. |
| 2003/0060112 A1 | 3/2003 | Rezai et al. |
| 2003/0105441 A1 | 6/2003 | Chmielewski |
| 2003/0114071 A1 | 6/2003 | Everhart et al. |
| 2003/0116888 A1 | 6/2003 | Rymer et al. |
| 2003/0118764 A1 | 6/2003 | Adams et al. |
| 2003/0129915 A1 | 7/2003 | Harriz |
| 2003/0134102 A1 * | 7/2003 | Wang et al. ............... 428/317.9 |
| 2003/0158531 A1 | 8/2003 | Chmielewski |
| 2003/0171729 A1 | 9/2003 | Kaun et al. |
| 2004/0019168 A1 * | 1/2004 | Soerens et al. .............. 526/271 |
| 2004/0054341 A1 | 3/2004 | Kellenberger et al. |
| 2004/0054342 A1 | 3/2004 | Newbill et al. |
| 2004/0116014 A1 | 6/2004 | Soerens et al. |
| 2004/0116287 A1 | 6/2004 | Wang et al. |
| 2004/0158212 A1 | 8/2004 | Ponomarenko et al. |
| 2004/0203308 A1 | 10/2004 | Ko et al. |
| 2004/0222568 A1 | 11/2004 | Armantrout et al. |
| 2005/0027268 A1 | 2/2005 | Qin et al. |
| 2005/0096435 A1 | 5/2005 | Smith et al. |
| 2005/0096623 A1 | 5/2005 | Nhan et al. |
| 2005/0101929 A1 | 5/2005 | Waksmundzki et al. |
| 2005/0107759 A1 | 5/2005 | Waksmundzki et al. |
| 2005/0124959 A1 | 6/2005 | Alcantara et al. |
| 2005/0137085 A1 | 6/2005 | Zhang et al. |
| 2005/0186351 A1 | 8/2005 | Fung et al. |
| 2005/0228350 A1 | 10/2005 | Ranganathan et al. |

| | | | |
|---|---|---|---|
| 2005/0256488 A1 | 11/2005 | Sperl | |
| 2006/0004336 A1 | 1/2006 | Zhang et al. | |
| 2006/0005919 A1 | 1/2006 | Schewe et al. | |
| 2006/0069365 A1 | 3/2006 | Sperl et al. | |
| 2006/0127688 A1* | 6/2006 | Busch et al. | 428/500 |
| 2006/0135932 A1 | 6/2006 | Abuto et al. | |

FOREIGN PATENT DOCUMENTS

| | | |
|---|---|---|
| EP | 0 497 072 A1 | 6/1988 |
| EP | 0 534 863 A1 | 5/1989 |
| EP | 0 572 033 B1 | 9/1989 |
| EP | 0 598 413 A1 | 11/1989 |
| EP | 0 492 554 A1 | 4/1990 |
| EP | 0 633 009 A2 | 7/1992 |
| EP | 0 700 672 A1 | 8/1992 |
| EP | 0 548 714 B1 | 9/1992 |
| EP | 0 700 673 A1 | 3/1993 |
| EP | 0 788 874 B1 | 5/1994 |
| EP | 0 794 751 B2 | 6/1994 |
| EP | 0 802 949 B1 | 1/1995 |
| EP | 0 947 549 A1 | 3/1996 |
| EP | 0 957 870 B1 | 3/1996 |
| EP | 0 601 610 A1 | 4/1997 |
| EP | 0 779 065 B1 | 4/1998 |
| EP | 1 013 291 A1 | 9/1999 |
| EP | 1 078 616 A2 | 10/1999 |
| EP | 0 179 937 B1 | 6/2000 |
| EP | 0 994 686 B1 | 6/2000 |
| EP | 0 270 058 A1 | 2/2001 |
| EP | 0 315 507 A2 | 2/2001 |
| EP | 0 324 097 B1 | 2/2001 |
| EP | 0 788 336 B1 | 4/2001 |
| EP | 1 245 209 A2 | 6/2002 |
| EP | 0 341 870 A2 | 10/2002 |
| EP | 1 285 643 A2 | 11/2002 |
| EP | 1 077 052 A1 | 1/2003 |
| EP | 0 471 114 B1 | 2/2003 |
| EP | 0 967 950 B1 | 3/2003 |
| EP | 1 077 053 A2 | 5/2003 |
| EP | 1 161 928 B1 | 5/2003 |
| EP | 0 333 209 A2 | 3/2004 |
| GB | 2 151 272 A | 7/1985 |
| GB | 2 273 659 A | 6/1994 |
| JP | 04-065568 A | 3/1992 |
| JP | 07-138866 A | 5/1995 |
| JP | 07-163620 A | 6/1995 |
| WO | WO 93/15249 A1 | 8/1993 |
| WO | WO 95/10995 A1 | 4/1995 |
| WO | WO 95/20931 A1 | 8/1995 |
| WO | WO 96/11107 A1 | 4/1996 |
| WO | WO 96/14885 A1 | 5/1996 |
| WO | WO 96/16624 A2 | 6/1996 |
| WO | WO 97/07761 A1 | 3/1997 |
| WO | WO 97/39780 A1 | 10/1997 |
| WO | WO 98/03710 A1 | 1/1998 |
| WO | WO 98/45519 A1 | 10/1998 |
| WO | WO 99/00093 A1 | 1/1999 |
| WO | WO 99/00095 A1 | 1/1999 |
| WO | WO 99/25393 A2 | 5/1999 |
| WO | WO 99/25745 A1 | 5/1999 |
| WO | WO 99/25748 A1 | 5/1999 |
| WO | WO 00/09058 A1 | 2/2000 |
| WO | WO 00/37000 A1 | 6/2000 |
| WO | WO 00/37009 A2 | 6/2000 |
| WO | WO 00/37735 A1 | 6/2000 |
| WO | WO 00/56959 A1 | 9/2000 |
| WO | WO 00/59438 A1 | 10/2000 |
| WO | WO 00/59439 A1 | 10/2000 |
| WO | WO 00/63295 A1 | 10/2000 |
| WO | WO 01/15650 A1 | 3/2001 |
| WO | WO 01/47456 A1 | 7/2001 |
| WO | WO 02/10032 A2 | 2/2002 |
| WO | WO 02/24132 A2 | 3/2002 |
| WO | WO 02/34184 A1 | 5/2002 |
| WO | WO 02/43784 A2 | 6/2002 |
| WO | WO 02/053378 A2 | 7/2002 |
| WO | WO 03/015560 A1 | 2/2003 |
| WO | WO 03/015682 A1 | 2/2003 |
| WO | WO 03/015684 A1 | 2/2003 |
| WO | WO 03/018671 A1 | 3/2003 |
| WO | WO 03/037392 A1 | 5/2003 |
| WO | WO 03/047485 A1 | 6/2003 |
| WO | WO 03/051411 A1 | 6/2003 |
| WO | WO 03/51417 A1 | 6/2003 |
| WO | WO 03/053297 A2 | 7/2003 |
| WO | WO 03/053319 A2 | 7/2003 |
| WO | WO 03/057268 A1 | 7/2003 |
| WO | WO 03/057964 A1 | 7/2003 |
| WO | WO 03/068122 A1 | 8/2003 |
| WO | WO 03/099186 A1 | 12/2003 |
| WO | WO 2004/084784 A1 | 10/2004 |
| WO | WO 2005/044163 A1 | 5/2005 |
| WO | WO 2007/070776 A2 | 6/2007 |

OTHER PUBLICATIONS

American Society for Testing Materials (ASTM) Designation: D 737-96, "Standard Test Method for Air Permeability of Textile Fabrics," pp. 207-211, published Apr. 1996.

American Society for Testing Materials (ASTM) Designation: D1238-70, "Standard Method for Measuring Flow Rates of Thermoplastics by Extrusion Plastometer," pp. 415-426, effective Jun. 1970.

American Society for Testing Materials (ASTM) Designation: D5035-90, "Standard Test Method for Breaking Force and Elongation of Textile Fabrics (Strip Force)," pp. 726-731, published May 1990.

American Society for Testing Materials (ASTM) Designation: F 316-03, "Standard Test Methods for Pore Size Characteristics of Membrane Filters by Bubble Point and Mean Flow Pore Test," pp. 1-7, published Apr. 2003.

Federal Test Method Standard (FTMS) No. 191A, Method 5450, "Permeability To Air; Cloth; Calibrated Orifice Method," Jul. 20, 1978, 5 pages.

INDA Standard Test Method IST 70.1 (92), "Standard Test Method for Air Permeability of Nonwoven Fabrics," pp. 93-101.

"Molecular Weight Distributions," *Encyclopedia of Polymer Science and Engineering*, Second Edition, vol. 3, John Wiley & Sons, New York, 1985, pp. 299-300.

Coates, Geoffrey W. And Robert M. Waymouth, "Oscillating Stereocontrol: A Strategy for the Synthesis of Thermoplastic Elastomeric Polypropylene," *Science*, vol. 267, Jan. 13, 1995, pp. 217-219.

Cowie, J.M.G., "Solubility and the Cohesive Energy Density," *Polymers: Chemistry and Physics of Modern Materials*, Intext Educational Publishers, New York, 1973, pp. 142-145.

Lawrence, K.D. et al., "An Improved Device for the Formation of Superfine, Thermoplastic Fibers," *NRL Report* 5265, U.S. Naval Research Laboratory, Washington, D.C., Feb. 11, 1959, pp. 1-7.

Neumann, A.W., and R.J. Good, "Techniques of Measuring Contact Angles," Chapter 2, *Surface and Colloid Science—Experimental Methods*, vol. 11, edited by R.J. Good and R.R. Stromberg, Plenum Press, 1979, pp. 31-91.

Wagener, K.B., "Oscillating Catalysts: A New Twist for Plastics," *Science*, vol. 267, Jan. 13, 1995, p. 191.

Wente, V.A. et al., "Manufacture of Superfine Organic Fibers," *NRL Report* 4364, U.S. Naval Research Laboratory, Washington, D.C., May 25, 1954, pp. 1-15.

* cited by examiner

STRETCHABLE ABSORBENT COMPOSITE WITH LOW SUPERABORBENT SHAKE-OUT

FIELD OF THE INVENTION

The present invention relates to an absorbent composite article. More particularly, the present invention pertains to an absorbent composite which can be incorporated in a personal care article, such as an absorbent feminine care article, adult incontinence article, children's training pant, infant diaper, or the like.

BACKGROUND OF THE INVENTION

Absorbent products intended to absorb discharged body fluids are well known in the art. Such absorbent products generally comprise a fibrous mass or other absorbent body which can absorb and hold the body fluids. Similarly, it is well known that, feminine care articles have been employed to absorb and hold liquids, such as urine, blood and/or menses. The absorbent articles have included various systems of liquid-handling layers, such as intake layers, distribution layers, retention layers and the like. The absorbent articles have also included operative amounts of superabsorbent materials to provide increased absorbent capacity. Additionally, the absorbent articles have included patterns of embossments distributed on the bodyside surface of the article to provide a hinging action, or to inhibit or direct a desired flow of liquids. Other arrangements of the absorbent articles have included wing portions which can help to hold the article in place at a selected location in a wearer's undergarment. Various fasteners have been employed to secure the wing portions in a desired configuration during ordinary use. The fasteners have included adhesive fasteners as well as interengaging mechanical fasteners, and the mechanical fasteners have included conventional, hook-and-loop fasteners. Particular arrangements of the various components of the absorbent articles have been configured to provide desired levels of extensibility or elastomeric stretchability.

Conventional absorbent systems, however, have not provided desired levels of stretchability in combination with desired levels of containment of superabsorbent particles in a fibrous matrix. When such conventional absorbent systems have been constructed to provide a composite which includes superabsorbent particles within a matrix of fibers, the composite has not adequately provided desired levels of stretchability and particle-containment. The particles of superabsorbent materials have not been adequately held and retained in the associated matrix of fibers, and the absorbent composite has exhibited excessive amounts of particle shake-out. As a result, such conventional system have required additional envelope structures of barrier materials to contain superabsorbent particles that have detached from composite, and to prevent the particles from contacting the body of a user.

BRIEF DESCRIPTION OF THE INVENTION

Generally stated, the present invention provides an article comprising a stretchable absorbent composite including a quantity of superabsorbent particles which are operatively contained within a matrix of elastomeric polymer fibers. In particular aspects, the composite article can include at least about 60 wt % of the superabsorbent particles and not more than about 40 wt % of the elastomeric polymer fibers, based on a total weight of the absorbent composite. In other aspects, the composite article can provide a high stretchability. Additional aspects of the composite article can be configured to provide a low shake-out. Particular configurations of the invention can provide a stretchability value of at least about 30%. Additional aspects can provide a shake-out value of not more than about 2%. In other aspects, the invention can provide a shake-out value of not more than about 1.2%. Further aspects of the absorbent composite can include superabsorbent particles having a coating of treatment-material that is thermally processible. Additional aspects can include a treatment-material which is water soluble.

By incorporating its various features and configurations in desired arrangements, the article of the invention can, for example, provide an improved absorbent composite having a desired combination of stretchability, absorbent capacity and particle-containment. The article can provide improved fit and comfort. The article can also be more efficiently manufactured by eliminating the need for additional barrier or containment components while also providing desired levels of absorbent capacity and stretchability.

BRIEF DESCRIPTION OF THE DRAWINGS

The various features, aspects and advantages of the present invention will become better understood with reference to the following description, appended claims and accompanying drawings where:

DETAILED DESCRIPTION OF THE INVENTION

Figure 1:
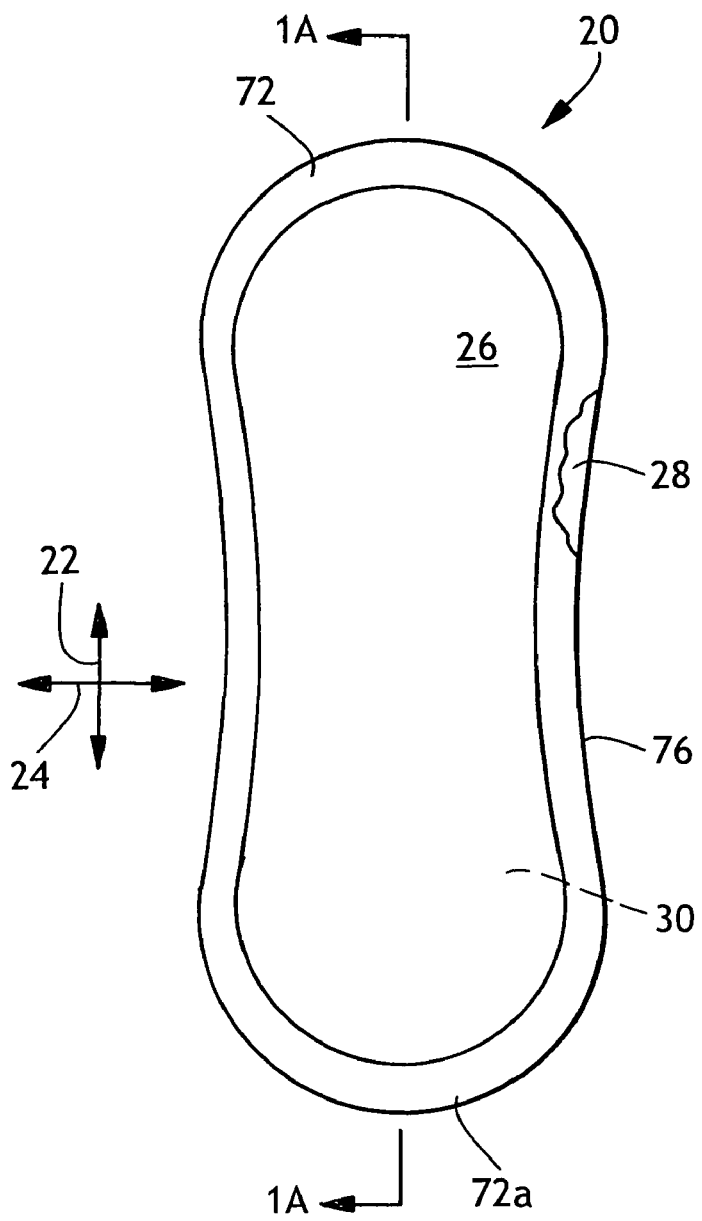
FIG. 1 shows a representative, partially cut-away, top, plan view of a bodyside of a representative personal care article which includes the absorbent composite of the invention.
Figure 1A:
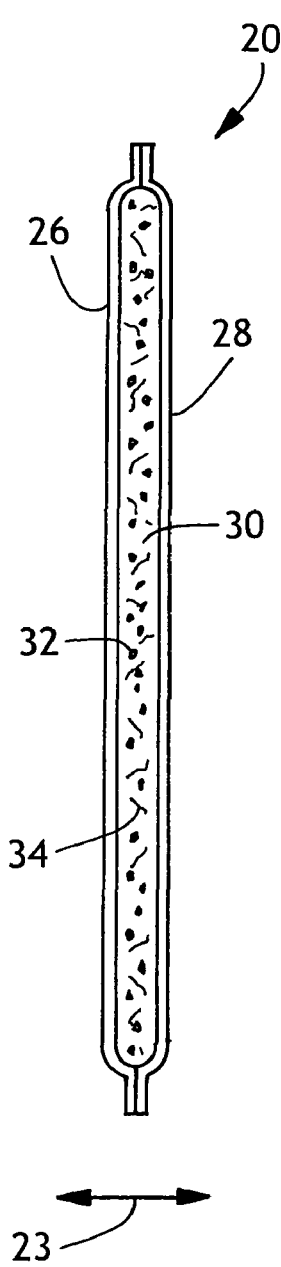
FIG. 1A shows a representative view of a longitudinal cross-section through the article representatively shown in FIG. 1.
Figure 2:
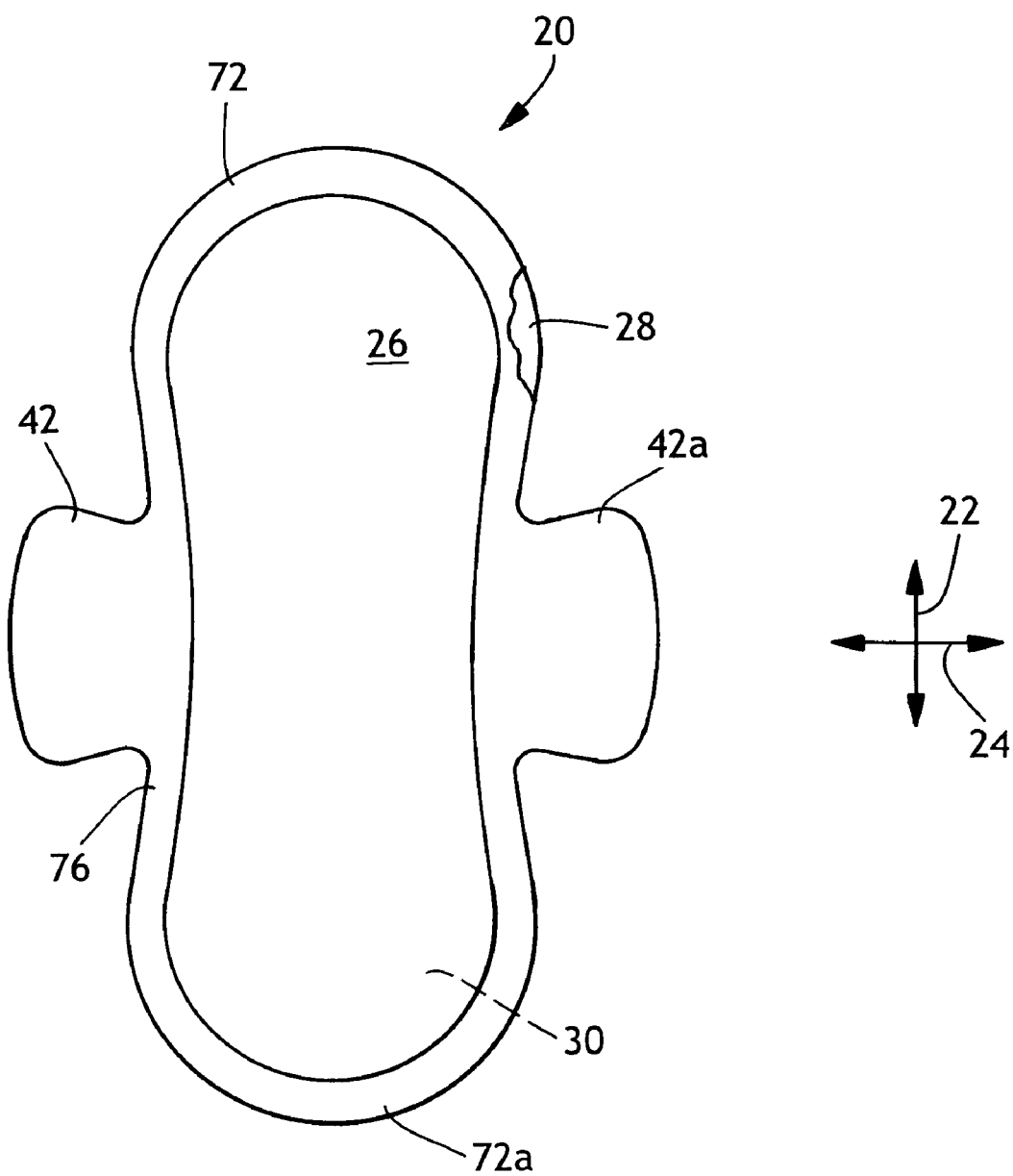
FIG. 2 shows a representative top, plan view of a bodyside of a representative personal care article which includes wing-type side panels.
Figure 3:
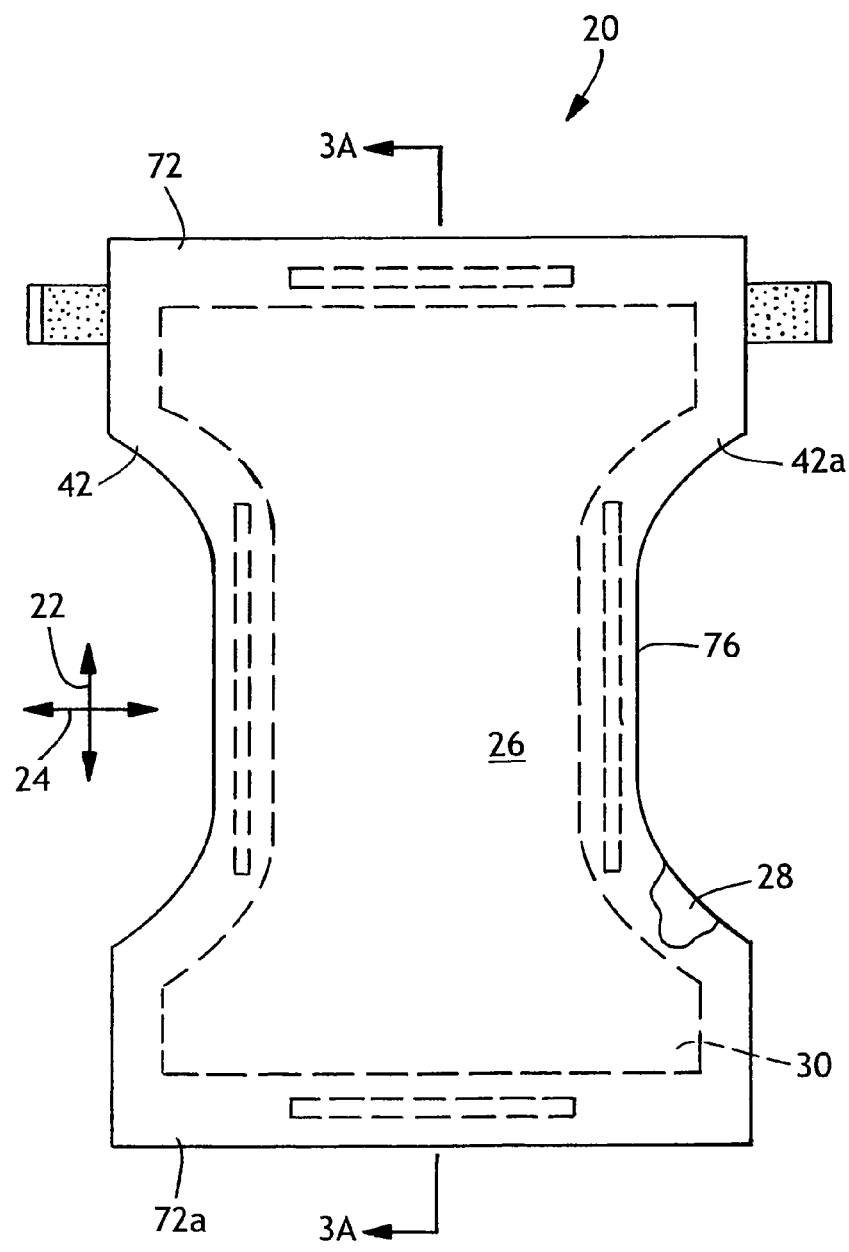
FIG. 3 shows a representative, partially cut-away, top, plan view of a bodyside of another representative personal care article which includes the absorbent composite of the invention.
Figure 3A:
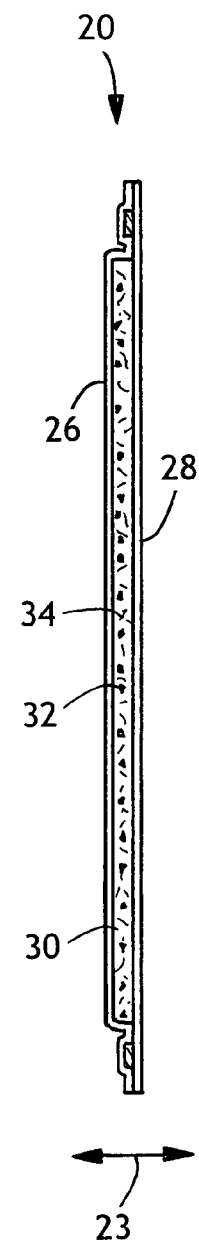
FIG. 3A shows a representative view of a longitudinal cross-section through the article representatively shown in FIG. 3.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

By the terms "particle", "particles", "particulate", "particulates" and the like, it is meant that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like.

Additionally, a particle, particulate or any desired agglomeration thereof may be composed of more than one type of material.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The coform material may also include other materials, such as superabsorbent particles. The meltblown fibers containing wood fibers are collected on a forming surface, such as provided by a foraminous belt. The forming surface may include a'gas-pervious material, such as spunbonded fabric material, that has been placed onto the forming surface.

"Elastomeric" and "elastic" are used interchangeably to refer to a material or composite that exhibits properties which approximate the properties of natural rubber. The elastomeric material is generally capable of being stretched or otherwise deformed, and then recovering a significant portion of its shape after the stretching or deforming force is removed.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible configurational isomers of the material. These configurations include, but are not limited to isotactic, syndiotactic and atactic symmetries.

The phrase "complex liquid" describes a liquid generally characterized as being a viscoelastic liquid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption, although some components of the simple liquids may be absorbed or adsorbed more readily than others.

Although a complex liquid is generally characterized herein as including specific components having inhomogeneous properties, each specific component of a complex liquid generally has homogeneous properties. Consider for example a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

The phrase "absorbent article" refers to devices which can absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles can include a liquid pervious topsheet, a backsheet joined to the topsheet, and an absorbent core positioned and held between the topsheet and the backsheet. The topsheet is operatively permeable to the liquids that are intended to be held or stored by the absorbent article, and the backsheet may or may not be substantially impervious or otherwise operatively impermeable to the intended liquids. The absorbent article may also include other components, such as liquid wicking layers, liquid intake layers, liquid distribution layers, transfer layers, barrier layers, wrapping layers and the like, as well as combinations thereof. Disposable absorbent articles and the components thereof can operate to provide a body-facing surface and a garment-facing surface. As used herein, a body-facing or bodyside surface means that surface of the article or component which is intended to be disposed toward or placed adjacent to the body of the wearer during ordinary use, while the outward, outward-facing or garment-side surface is on the opposite side, and is intended to be disposed to face away from the wearer's body during ordinary use. Such outward surface may be arranged to face toward or placed adjacent to the wearer's undergarments when the absorbent article is worn.

FIGS. 1 through 3A, illustrate examples of a suitable article 20, such as the representatively shown personal care, absorbent articles, which can be configured to incorporate the present invention. The article can comprise an absorbent body structure, and the absorbent body can include an absorbent composite component 30. Desirably, the absorbent composite has a significant amount of stretchability and includes particles of superabsorbent material (SAM). Additionally, the superabsorbent particles can be operatively contained within a matrix of fibers. Accordingly, the article can comprise a stretchable absorbent composite 30 that includes a quantity of superabsorbent particles 32 which are operatively contained with a matrix of fibers. Desirably, the fibrous matrix can include an operative amount of elastomeric polymer fibers 34. In particular aspects, the composite 30 can include at least about 60 wt % of the superabsorbent particles, and not more than about 40 wt % of the elastomeric polymer fibers, based on a total weight of the composite. In other aspects, the stretchable composite can provide a high stretchability value. Additional aspects of the stretchable composite can include a configuration that provides a distinctively low shake-out value. Particular configurations of the invention can, for example, provide a stretchability of at least about 30%.

Another aspect of the invention can include a configuration which provides a shake-out value of not more than about 2%. In still other aspects, the invention can provide a shake-out value of not more than about 1.2%, not more than about 1%, or not more than about 0.5%. Further aspects of the absorbent composite of the invention can include superabsorbent particles having a coating of treatment-material that is thermally processable. Additional aspects can include a treatment-material which is water soluble.

In desired arrangements, for example, the article 20 and its associated components (e.g. absorbent composite 30) can have a lengthwise longitudinal direction 22 along an appointed y-axis of the article, a transverse, laterally extending, cross-direction 24 along an appointed x-axis of the article, and a thickness dimension along an appointed z-direction 23 of the article. Additionally the article can include first and second longitudinally opposed end portions 72 and 72a, and an intermediate portion 76 located between the end portions. As representatively shown, the longitudinal dimension of the article is relatively larger than the lateral dimension of the article. The article 20 may further include a bodyside cover or topsheet 26, and an outercover baffle or backsheet 28. The absorbent structure can be positioned between the topsheet and backsheet components, and the topsheet and backsheet may or may not be substantially co-terminus. Particular configurations can include a topsheet and backsheet that extend beyond the terminal edges of the absorbent body, and the extending portions of the topsheet and backsheet can be attached to each other to provide a perimeter bond. In desired arrangements, the topsheet can be liquid-permeable, and the backsheet can be operatively liquid-impermeable. In still other aspects, the absorbent body structure can include an elastomeric absorbent composite 30, and may further include additional absorbent components, such as an intake component, a distribution component, a shaping component, a retention component or the like, as well as combinations thereof. Any or all of the components employed in the article may be configured to have elastomeric properties that are similar to those exhibited by the stretchable absorbent composite 30. The various components, particularly the absorbent components, can have corresponding configurations of absorbent capacities, configurations of densities, configurations of basis weights and/or configurations of sizes which are selectively constructed and arranged to provide desired combinations of liquid intake time, absorbent saturation capacity, absorbent retention capacity, liquid distribution along the thickness and x-y directions of the article, shape maintenance, and aesthetics.

By incorporating its various features and configurations, alone and in operative combinations, the article of the invention can provide an improved absorbent composite having a desired combination of stretchability, absorbent capacity and particle-containment. The article can be less susceptible to premature leakage, and can provide improved comfort and fit, improved protection and increased confidence to the wearer. Additionally, the article can be more efficiently manufactured to provide desired levels of absorbent capacity and low shake-out of particles. For example, the article can help eliminate the need for additional barrier or wrapping components to contain excessive amounts of loose superabsorbent particles.

The absorbent composite component 30 can include an operative amount of elastomeric polymer fibers. In a particular aspect, the amount of elastomeric polymer fibers can be at least a minimum of about 5 wt %, based on the total weight of the stretchable absorbent composite 30. The amount of polymer fibers can alternatively be at least about 7 wt % and can optionally be at least about 10 wt % to provide desired benefits. In another feature, the amount of elastomeric polymer fibers can be not more than a maximum of about 40 wt %. The amount of polymer fibers can alternatively be not more than about 25 wt %, and can optionally be not more than about 15 wt % to provide improved benefits.

If the amount of elastomeric polymer fibers is outside the desired values, various disadvantages can occur. An insufficient amount of meltblown polymer fiber may provide an inadequate level of structural integrity, and an inadequate ability to stretch and retract elastomerically. An excessively high amount of meltblown fiber may hold the superabsorbent particles too tightly and may not allow a sufficient amount of swelling. The restricted swelling of the superabsorbent particles can excessively limit the absorbent capacity of the composite. Where the meltblown polymer is generally hydrophobic, an excessively large amount of meltblown fiber may undesirably limit the intake rate at which the composite acquires liquid, and may limit the distribution of liquid to other parts of the absorbent composite.

The elastomeric material of the polymer fibers may include an olefin elastomer or a non-olefin elastomer, as desired. For example, the elastomeric fibers can include olefinic copolymers, polyethylene elastomers, polypropylene elastomers, polyester elastomers, polyisoprene, cross-linked polybutadiene, diblock, triblock, tetrablock, or other multi-block thermoplastic elastomeric and/or flexible copolymers such as block copolymers including hydrogenated butadiene-isoprene-butadiene block copolymers; stereoblock polypropylenes; graft copolymers, including ethylene-propylene-diene terpolymer or ethylene-propylene-diene monomer (EPDM) rubber, ethylene-propylene random copolymers (EPM), ethylene propylene rubbers (EPR), ethylene vinyl acetate (EVA), and ethylene-methyl acrylate (EMA); and styrenic block copolymers including diblock and triblock copolymers such as styrene-isoprene-styrene (SIS), styrene-butadiene-styrene (SBS), styrene-isoprene-butadiene-styrene (SIBS), styrene-ethylene/butylene-styrene (SEBS), or styrene-ethylene/propylene-styrene (SEPS), which may be obtained from Kraton Inc. of Houston, Tex., under the trade designation KRATON elastomeric resin or from Dexco, a division of ExxonMobil Chemical Company, under the trade designation VECTOR (SIS and SBS polymers); blends of thermoplastic elastomers with dynamic vulcanized elastomer-thermoplastic blends; thermoplastic polyether ester elastomers; ionomeric thermoplastic elastomers; thermoplastic elastic polyurethanes, including those available from E. I. Du Pont de Nemours Co., under the trade name LYCRA polyurethane, and ESTANE available from Noveon, Inc.; thermoplastic elastic polyamides, including polyether block amides available from Ato Chemical Company, under the trade name PEBAX polyether block amide; thermoplastic elastic polyesters, including those available from E. I. Du Pont de Nemours Co., under the trade name HYTREL, and ARNITEL from DSM Engineering Plastics of Evansville, Ind., and single-site or metallocene-catalyzed polyolefins having a density of less than about 0.89 grams/cubic centimeter, available from Dow Chemical Co. under the trade name AFFINITY; and combinations thereof.

As used herein, a tri-block copolymer has an ABA structure where the A represents several repeat units of type A, and B represents several repeat units of type B. As mentioned above, several examples of styrenic block copolymers are SBS, SIS, SIBS, SEBS, and SEPS. In these copolymers the A blocks are polystyrene and the B blocks are a rubbery component. Generally these triblock copolymers have molecular weights that can vary from the low thousands to hundreds of thousands and the styrene content can range from 5% to 75% based on the weight of the triblock copolymer. A diblock copolymer is similar to the triblock but is of an AB structure. Suitable diblocks include styrene-isoprene diblocks, which have a molecular weight of approximately one-half of the triblock molecular weight having the same ratio of A blocks to B blocks.

In desired arrangements, the polymer fibers can include at least one material selected from the group consisting of styreneic block copolymers, elastic polyolefin polymers and co-polymers and EVA/AMA type polymers.

In particular arrangements, for example, the elastomeric material of the polymer fibers can include KRATON blend G 2755 from Kraton Inc.; and various commercial grades of low crystallinity, lower molecular weight metallocene polyolefins available from ExxonMobil Chemical Company under the VISTAMAXX trade designation. The KRATON material is believed to be a blend of styrene ethylene-butylene styrene polymer, ethylene waxes and tackifying resins. The VISTAMAXX material is believed to be metallocene propylene ethylene co-polymer.

In another feature, the polymer fibers include an operative amount of a surfactant. The surfactant can be combined with the polymer fibers in any operative manner. Various techniques for combining the surfactant are conventional and well known to persons skilled in the art. For example, the surfactant may be compounded with the polymer employed to form the meltblown fibers. In a particular feature, the surfactant may be configured to operatively migrate or segregate to the outer surface of the fibers upon the cooling of the fibers. Alternatively, the surfactant may be applied to or otherwise combined with the polymer fibers after the fibers have been formed.

The polymer fibers include an operative amount of a surfactant, based on the total weight of the fibers and surfactant. In particular aspects, the polymer fibers can include at least a minimum of about 0.1 wt %, as determined by water extraction. The amount of surfactant can alternatively be at least about 0.15 wt %, and can optionally be at least about 0.2 wt % to provide desired benefits. In other aspects, the amount of surfactant can be generally not more than a maximum of about 2 wt %. The amount of surfactant can alternatively be not more than about 1 wt %, and can alternatively be not more than about 0.5 wt % to provide improved performance.

If the amount of surfactant is outside the desired ranges, the various disadvantages can occur. For example, an excessively low amount of surfactant may not allow the hydrophobic meltblown fibers to wet with the absorbed liquid. An excessively high amount of surfactant may allow the surfactant to wash off from the fibers and undesirably interfere with the ability of the composite to transport liquid. Where the surfactant is compounded or otherwise internally added to the elastomeric polymer, an excessively high level of surfactant can create conditions that cause a poor formation of the polymer fibers.

In desired configurations, the surfactant can include at least one material selected from the group that includes polyethylene glycol ester condensates and alkyl glycoside surfactants. For example, the surfactant can be a GLUCOPON surfactant which can be composed of 40% water, and 60% d-glucose, decyl, octyl ethers and oligomerics.

A particular example of a sprayed-on surfactant can include a water/surfactant solution which includes 16 L of hot water (about 45° C. to 50° C.) mixed with 0.20 Kg of GLUCOPON 220 UP surfactant and 0.36 Kg of ALCHOVEL Base N-62 surfactant. This is a 1:3 ratio of the GLUCOPON 220 UP surfactant to the ALCHOVEL Base N-62 surfactant. GLUCOPON 220 UP is available from Cognis Corporation, a business having offices located in Cincinnati, Ohio, U.S.A. ALCHOVEL Base-N62 is available from Uniqema, a business having offices located in New Castle, Del., U.S.A. When employing a sprayed-on surfactant, a relatively lower amount of sprayed-on surfactant may be desirable to provide the desired containment of the superabsorbent particles. Excessive amounts of the liquid surfactant may hinder the desired attachment of the superabsorbent particles to the molten, elastomeric meltblown fibers.

An example of an internal surfactant or wetting agent that can be compounded with the elastomeric fiber polymer can include a MAPEG DO 400 PEG (polyethylene glycol) ester. This material is available from BASF, a business having offices located in Freeport, Tex., U.S.A. Other internal surfactants can include a polyether, a fatty acid ester, a soap or the like, as well as combinations thereof.

In particular feature, an operative amount of the polymer fibers can have a fiber diameter of not less than a minimum of about 8 microns (μm). Another feature can have a configuration in which an operative amount of the polymer fibers have a fiber diameter of not more than a maximum of about 20 μm. In a further feature, not more than 20 wt % and desirably, not more than about 15 wt % of the meltblown, elastomeric polymer fibers in the absorbent composite 30 have a fiber diameter of less than 8 μm. Still another feature can have a configuration in which not more than about 20 wt % and desirably, not more than about 15 wt % of the elastomeric polymer fibers have a fiber diameter greater than about 20 μm.

If the amount or proportion of the small polymer fibers (fiber diameter less than about 8 μm) is too great, the absorbent composite 30 may exhibit inadequate levels of stretchability. An overly great amount of the small polymer fibers may also excessively tie down the superabsorbent particles and not allow a desired amount of swelling in the superabsorbent particles. Additionally the smaller fibers can become stress crystallized, and the tensions (modulus) of the stretchable composite 30 can be too high.

If the amount or proportion of large polymer fibers (fiber diameter greater than about 20 μm) is too great, the absorbent composite 30 may exhibit inadequate levels of particle containment. The meltblown elastomeric fibers may not provide a sufficient amount of fiber surface area, and the superabsorbent particles, may not be adequately contained and held in the matrix of elastomeric, polymer fibers.

In another feature, the elastomeric polymer fibers can be produced from a polymer material having a selected melt flow rate (MFR). In a particular aspect, the MFR can be up to a maximum of about 300. Alternatively, the MFR can be up to about 230 or 250. In another aspect, the MFR can be a minimum of not less than about 20. The MFR can alternatively be not less than about 100, and can optionally be not less than about 175 or 180 to provide desired performance. The described melt flow rate has the units of grams flow per 10 minutes (g/10 min). The parameter of melt flow rate is well known and can be determined by conventional techniques, such as by employing test ASTM D-1238-70 "extrusion plastometer" Standard Condition "L" 230° C. and 2.16 kg applied force.

A further feature of the stretchable absorbent composite can include a configuration in which a relatively low, normalized load value is needed to provide a desired strain elongation. Desired arrangements of the stretchable absorbent composite can be configured to include fibers formed from selected elastomeric materials. When such elastomeric material is formed into a meltblown fibrous web, the resulting, fibrous web can provide a low normalized load when stretched. In a desired feature, the stretchable, fibrous web formed from the elastomeric material can provide a strain elongation of at least about 30%. The low normalized load value of the fibrous web may also be provided at greater levels of elongations. Desirably, the low normalized load value can continue to be provided at strains of up to about 100%. For purposes of the present disclosure, the load is normalized to 1-inch (2.54 cm) of width and to 65 grams per square meter of basis weight—g/inch, normalized with respect to each 65 g/m² increment of basis weight of the meltblown web (g/inch):

(load in grams÷sample width in inches)*(65 g/m²÷sample basis weight in g/m²)

In a particular aspect, the normalized load value can be not more than a maximum of about 300 g/inch. The normalized load can alternatively be not more than about 250 g/inch, and can optionally be not more than about 210 g/inch to provide desired performance. The normalized, load value represents a retractive, tensile load in grams-force generated by a meltblown web which includes the identified polymer. Examples of the normalized load values provided by meltblown webs constructed from selected elastomeric materials are set forth in Table A.

TABLE A

| Polymer | Load at 100% Elongation: g/inch per 65 g/m² of basis weight (g/inch) |
|---|---|
| KRATON G2755 | 141.83 |
| PLTD 1723, 2.2 psig | 368.48 |
| PLTD 1723, 4 psig | 419.40 |
| PLTD 1776, 2.2 psig | 315.58 |
| PLTD 1776, 4 psig | 356.95 |
| PLTD 1777, 2.2 psig | 253.63 |
| PLTD 1777, 4 psig | 299.74 |
| PLTD 1778, 2.2 psig | 201.36 |
| PLTD 1778, 4 psig | 233.59 |

PLTD = Propylene-based developmental elastomer available from ExxonMobil Chemical Company, Houston, Texas, U.S.A.

The tension values in Table A provide a version of the modulus for the meltblown web. It can be noted that a web made with an olefin elastomer, such as the PLTD 1778 grade of olefin polymer, can exhibit a retractive force that approaches the low retractive force of a web made with KRATON synthetic rubber. In addition, it can be noted that the retractive tension load is affected by the draw force placed on the fiber as the fiber is formed during the meltblowing operation, as provided by the primary air pressure that is set forth in pounds per square inch gauge (psig) next to each polymer code designator. Additionally, it is noted that the higher primary air pressure values can generate a somewhat smaller diameter fiber.

The polymer fibers can be produced from a quantity of molten polymer (polymer-melt) which has been processed at a distinctive melt-temperature. In a particular aspect, the melt-temperature can be at least a minimum of about 200° C., or about 204° C. (about 400° F.). The melt-temperature can alternatively be at least about 235° C., and can optionally be at least about 240° C. to provide improved performance. In other aspects, the melt-temperature can be up to a maximum of about 268° C. (about 515° F.) or 315° C., or more. The melt-temperature can alternatively be up to about 260° C., and can optionally be up to about 255° C. to provide desired effectiveness.

The selected melt-temperatures can help the polymer fibers stay operatively soft and sticky for a longer time period after the molten fibers have departed the meltblowing die. This longer time can allow an increased penetration of the superabsorbent particles into the soft, hot polymer material, and can allow the polymer fibers to finish solidifying and quenching with the superabsorbent particles attached to the polymer fibers. If the melt-temperature is too low, the coated superabsorbent particles may not properly activate and adhere to the meltblown fibers. If the melt-temperature is too high, the meltblown fibers may exhibit poor formation and/or may exhibit excessively reduced stretch properties.

Additionally, the melt-temperature is appropriately regulated to be less than a degradation temperature at which the desired properties of elastomeric polymer material begin to excessively deteriorate. In particular configurations, for example, the elastomeric polymer material can have a degradation-temperature of not less than a minimum of about 315° C. (about 600° F.).

The absorbent structure (e.g. absorbent composite 30) can also include a significant amount of base superabsorbent material (e.g. the superabsorbent prior to any desired surface treatment described in the present disclosure), and the base superabsorbent material can desirably be in the form of particles or particulates. Superabsorbent materials suitable for use in the present invention are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 15 times, desirably at least about 20 times, more desirably at least about 40 times, and possibly about 60 times or more its weight in physiological saline (e.g. 0.9 wt % sodium chloride). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, chitosan salt, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyvinyl amines, polyquaternary ammonium, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are desirably lightly crosslinked to render the material substantially water insoluble. Crosslinking may, for example, be by irradiation or covalent, ionic, Van der Waals, or hydrogen bonding. Suitable base superabsorbent materials are available from various commercial vendors, such as the Dow Chemical Company, Degussa Superabsorber, Inc., BASF Inc. and others. The superabsorbent material may desirably be included in an appointed storage or retention portion of the absorbent system, and may optionally be employed in other components or portions of the absorbent article.

The amount of superabsorbent material in the absorbent composite 30 can be at least a minimum of about 60 wt %, as determined with respect to the total weight of the composite. The amount of superabsorbent material can alternatively be at least about 65 wt %, and can optionally be at least about 70 wt % or 75 wt % to provide improved benefits. In other aspects, the amount of superabsorbent material can be up to a maximum of about 95 wt %, or more. The amount of superabsorbent material can alternatively be up to about 90 wt %, and can optionally be up to about 85 wt % to provide desired effectiveness.

If the amount of superabsorbent is outside the desired values, the absorbent composite may have an inadequate combination of high absorbent capacity and low bulk. Large levels of other absorbent materials, such as woodpulp may be needed to provide the desired level of absorbency, and these other materials can excessively increase the thickness of the absorbent composite, and can excessively decrease stretchability of the composite.

The superabsorbent particles can further include a distinctive surface treatment material. In a particular aspect, the surface treatment can include an operative coating with the surface treatment material. In a particular aspect, the surface treatment can include a polymer that is thermally processible. In another aspect, the surface treatment can include a polymer that is water soluble. The coating may be discontinuous or substantially continuous, as appropriate for providing an operative surface treatment of the superabsorbent particles.

Generally stated, the treatment-material can desirably have a melt-temperature which is greater than the temperature of the air or other gas that carries the superabsorbent particles to the appointed web forming area. The coating polymer can desirably provide an operative amount of stickiness at temperatures above the melting-point or softening-point of the coating polymer. In a desired feature, the surface treatment material can have a treatment-material melting-point temperature which is at least a minimum of about 60° C. Accordingly, the treatment material can suitably activate and soften to become operatively sticky during the meltblown web-forming process, and the superabsorbent particles can more effectively attach to the fibers incorporated in the formed web of absorbent composite material. The treatment material can alternatively have a melting-point temperature of at least about 70° C., and can optionally have a melting-point temperature of at least about 80° C. In another feature, the melting-point temperature of the treatment-material can be up to about 100° C., or more. In further aspects, the treatment-material, melting-point temperature can be not more than about 220° C., and alternatively, can be not more than about 150° C. to provide improved performance.

If the melting-point temperature of the treatment material is outside the desired values, the treated superabsorbent particles may excessively stick together and undesirably agglomerate. The excessively stuck-together particles of superabsorbent can undesirably reduce the efficiency and effectiveness of the web-forming process employed to produce the absorbent composite 30.

The surface treatment can also include a polymer that is hydrophilic and water soluble. In a particular feature, the coating polymer can be solution-coated onto the superabsorbent particles by employing any operative application technique. Such solution coating techniques are conventional and well known in the art. The water solubility of the coating polymer can advantageously help to provide greater cohesion between the coating polymer and the particulate superabsorbent. The greater cohesion can then more effectively cooperate with the thermal processibility of the coating polymer. As a result, the superabsorbent particles can be more effectively held and contained with the matrix of elastomeric polymer fibers.

The base superabsorbent materials can be operatively surface treated with a treatment material that includes one or more agents that exhibit desired thermoplastic properties. The selected agent or agents on the surface of the treated superabsorbent materials can operatively soften or melt upon heating; e.g. upon contacting hot air or the hot surfaces of other objects during the melt blowing process described herein. The heated surface-treatment material can operatively form bonds with the fibers incorporated in the absorbent composite, such as the thermoplastic elastomeric fibers and cellulosic wood pulp fibers. Accordingly, the surface treating material can promote a melt blown interaction among all of the components employed in the process of producing the absorbent composite 30. The surface treatment material can help to significantly enhance the retention of the superabsorbent particle retention, and help reduce the shake-out of superabsorbent particles.

Any operative thermoplastic agent can be incorporated into the surface treatment material that is coated onto the surface of superabsorbent materials to enhance thermal stickiness. A particular aspect of the invention can include a surface treatment material which has been configured to provide a superabsorbent material having a desired Thermal Stickiness Index (TSI) value, which is further described in the TEST METHODS section of the present disclosure. A particular feature of the invention can include a superabsorbent material which exhibits a TSI value of at least about 40. The TSI value can alternatively be at least about 60, and can optionally be at least about 80 to provide improved benefits. If the TSI parameter is outside the desired values, there can be insufficient attachment between the superabsorbent particles and the fibers in the absorbent composite 30. As a result, the absorbent composite can exhibit excessive amounts of particulate shake-out.

In conventional structures, surface coated superabsorbents have incorporated hydrophobic, thermoplastic coating materials, such as polyolefin surface coatings. Such surface treated superabsorbents, however, did not exhibit desired levels of stickiness and bonding integrity. To overcome the difficulties of the prior arrangements of coated superabsorbents, the present invention can be configured to incorporate one or more of the aspects and features set forth in the present disclosure.

In a particular feature, the surface treatment material can include a hydrophilic thermoplastic polymer, which is a thermally processible. Another feature of the invention can incorporate a surface treatment material which includes water soluble polymer. In a further feature, the invention can include a solution coating process which places the treatment material on the superabsorbent particle and promotes strong bonds between the coating and the particles. Various distinctive factors can influence the effectiveness of thermal stickiness provide by the surface coating. Such factors can, for example, include the cohesion strength of the selected, thermally-sticky coating material; the bond strength provided by the coating material; and the total number of bonds formed by the surface coating material. A thermally processible coating polymer with low cohesion can provide inadequate integrity and inadequate shake-out resistance even if perfect bonds are formed between the superabsorbent particles and adjacent particles or fibers. For example, wax is a thermally meltable polymer but provides insufficient cohesion. The low cohesion wax material is very easy torn apart and its corresponding bonds are easily breakable. Bond strength refers to the total energy required to separate bonds at the interface between two materials. In general, materials in the same nature tend to have higher bond strength. For example, a hydrophilic polymer forms stronger bonds with another hydrophilic polymer than with a hydrophobic polymer.

An important interfacial structure between two polymers which can help enhance bonding integrity is a structure that has been referred to by the nomenclature of an Interpenetrating Polymer Network (IPN). IPN pertains to macromolecular chains of a polymer which penetrate through the interface into another polymer domain, or vice versa. Such a penetrating network can promote bond strength, and typically occurs only between compatible polymers. The process employed to coat one polymer onto the other may affect the formation of the desired IPN structure. For example, when a thermally processible and water-soluble polymer (e.g., a hydroxypropyl cellulose, HPC, or a polyethylene oxide, PEO) is coated or otherwise applied onto a base superabsorbent polymer (e.g., a crosslinked sodium polyacrylate), there are two primary coating techniques. One application technique is to spray fine droplets of molten HPC or PEO onto the surface of superabsorbent particles. A second technique is to dissolve the HPC or PEO into water to form a solution, and then mix the solution with dry superabsorbent particles to allow the particles to absorb the solution. The first technique typically produces a coating with no IPN formation. The second technique can promote the formation of the IPN at the interface between the superabsorbent particle and the surface coating material due to a swelling of the superabsorbent, and a diffusion and penetration of water molecules into superabsorbent particles during the operation of the coating technique.

The factor which relate to the total numbers of bonds formed in the absorbent composite can depend upon the morphology of the coating material. When a hydrophobic polymer material is coated onto the surface of a superabsorbent particle, the hydrophobic polymer tends to form droplets on the particle surface due to a lack of compatibility between the superabsorbent polymer material and the coating polymer material. Such morphology can result in a low efficiency of utilization of the coating polymer (such efficiency is proportional to the coated surface area covered by the coating material). A hydrophilic coating material (e.g., a polymer that is hydrophilic, thermally processible and water soluble) can have greater compatibility with the superabsorbent polymer, and can be more capable of forming a more extensive thin layer of the coating material. The coating layer can cover the whole (or approximately the whole) outer-surface of the superabsorbent particle when the particle is coated by a solution coating process. The resulting morphology can produce a significantly larger amount of particle surface area that is coated by the thermally sticky coating material which employing a reduced amount of the coating material. As a result, the coating material can be utilized with significantly higher efficiency. The higher utilization efficiency of the coating material can increase the number of bonds formed between a superabsorbent particle and other particles and/or fibers in the absorbent composite.

The superabsorbent particles can, for example, also include a surface treatment material which is thermally processible. Additionally, the surface treatment material can be water soluble The thermally processible and water soluble coating materials (e.g. coating polymers) have a melting or softening temperature (i.e., $T_m$) and are capable of dissolving in water. Suitable thermally processible and water soluble polymers include, but are not limited to, modified polyvinyl alcohol, polyethylene oxide, polypropylene oxide, ethylene oxide-propylene oxide copolymer, polyethylene glycol, polypropylene glycol, ethylene glycol-propylene glycol copolymer, polyacrylic acid copolymers, quaternary ammonium acrylate, methacrylate, or acrylamide copolymers, modified polysaccharides, such as hydroxypropyl cellulose, methyl cellulose, methyl ethyl cellulose, polyethylene imine, as well as mixtures or other combinations thereof. The molecular weight of the selected polymer can be important. In general, a higher molecular weight polymer can provide a desired, higher intrinsic cohesion. When the molecular weight of a coating polymer is too high, however, an aqueous solution of the coating polymer can have an excessive level of viscosity, which may potentially create difficulties in conducting desired surface treating operations. In a particular aspect of the invention, the molecular weight of a thermally processible and water soluble surface treatment (e.g. coating) polymer can be at least a minimum of about 5,000. The molecular weight can alternatively be at least about 10,000, and can optionally be about 50,000. In another aspect the molecular weight of the surface treatment material can be up to a maximum of about 10,000,000. The molecular weight can alternatively be not more than about 1,000,000, and can optionally be not more than about 500,000 to provide improved benefits.

As previous mentioned, the thermally processible and water soluble, surface treatment material can desirably be coated onto the surface of the superabsorbent particle by employing an aqueous solution of the surface treatment material to promote the formation of a desired IPN. When the surface treatment material (e.g. polymer) is dissolved into an operative aqueous solution, the solution can have a selected concentration of the surface treatment material. In a particular feature, the concentration of the surface treatment material in the solution can be at least a minimum of about 0.01 wt %. The concentration of the surface treatment material can alternatively be at least about 0.1 wt %, and can optionally be at least about 0.5 wt % to provide improved benefits. In other aspects, the concentration of the surface treatment material can be up to a maximum of about 20 wt %, or more. The concentration of the surface treatment material can alternatively be up to about 10 wt %, and can optionally be up to about 5 wt % to provide improved effectiveness.

If the molecular weight and/or concentration of the surface treatment material outside the desired values, the treatment material may not adequately provide a desired, deeper penetration of the coated polymer into the superabsorbent polymer material. As a result, the superabsorbent material may exhibit insufficient levels of thermal stickiness, bonding strength and absorbency.

A selected amount of the thermally processible and water soluble, surface treatment material can be coated onto the surfaces of a superabsorbent particles to provide a desired, overall thermal stickiness of the coated superabsorbent particles.

In a particular aspect, the coating amount can be at least a minimum of about 0.1 wt %, as determined with respect to the total dry weight of the coated superabsorbent material. The coating amount can alternatively be at least about 0.3 wt %, and can optionally be at least about 0.5 wt % to provide improved benefits. In other aspects, the coating amount of the surface treatment material can be up to a maximum of about 10 wt %, or more. The coating amount can alternatively be up to about 7 wt %, and can optionally be up to about 5 wt % to provide improved effectiveness.

The surface treated superabsorbent material can retain a selected level of high absorbency. In a particular aspect, the surface treated superabsorbent particles can exhibit a centrifuge retention capacity (CRC) of at least about 15 g/g. The centrifuge retention capacity can alternatively be at least about 20 g/g, and can optionally be at least about 25 g/g to provide improved performance. The centrifuge retention capacity test is described in detail in the TEST METHODS section of the present disclosure.

The elastomeric absorbent composite can further include a definite, discrete amount of hydrophilic fibers, such as cellulose or cellulosic fibers. The amount of hydrophilic fibers may be in an amount greater than 0 wt %, and in particular configurations of the invention, can be at least about 5 wt % or 7 wt % to provide desired benefits. In another aspect, the amount of cellulosic or other hydrophilic fibers can be up to a maximum of about 35 wt %, based upon the total weight of the elastomeric absorbent composite. The amount of hydrophilic fibers can alternatively be up to a maximum of about 25 wt %, and can optionally be up to about 15 wt %.

The selected amounts of cellulosic or other hydrophilic fiber can help provide increased levels of liquid intake and wicking. Excessive amounts of hydrophilic fibers, however, can undesirably reinforce the composite structure and excessively limit properties such as elasticity, stretch and recovery. Additionally, overly large amounts of the hydrophilic fiber can lead to excessive cracking of the absorbent composite during extension and stretching.

The cellulosic fibers may include, but are not limited to, chemical wood pulps such as sulfite and sulfate (sometimes called Kraft) pulps, as well as mechanical pulps such as ground wood, thermomechanical pulp and chemithermomechanical pulp. More particularly, the pulp fibers may include cotton, typical wood pulps, cellulose acetate, rayon, thermomechanical wood pulp, chemical wood pulp, debonded chemical wood pulp, milkweed floss, and combinations thereof. Pulps derived from both deciduous and coniferous trees can be used. Additionally, the cellulosic fibers may include such hydrophilic materials as natural plant fibers, cotton fibers, microcrystalline cellulose, microfibrillated cellulose, or any of these materials in combination with wood pulp fibers. Suitable cellulosic fibers can, for example, include: NB 416 a bleached southern softwood Kraft pulp (which is available from Weyerhaeuser Co., a business having offices located in Federal Way, Wash., U.S.A.); CR 54 a bleached southern softwood Kraft pulp (which is available from Bowater Inc., a business having offices located in Greenville S.C., U.S.A.); SULPHATATE HJ a chemically modified hardwood pulp (which is available from Rayonier Inc., a business having offices located in Jesup Ga., U.S.A.); NF 405 a chemically treated bleached southern softwood Kraft pulp (which is available from Weyerhaeuser Co.); and CR 1654 a mixed bleached southern softwood and hardwood Kraft pulp (which is available from Bowater Inc.). Desired configurations of the absorbent composites of the invention can, for example, include a pulp fiber content which is in the range of about 0 to 35 wt %.

In a further feature, the formed absorbent composite having the elastomeric fibers and superabsorbent particles can be subjected to a post heat-treatment to help improve the containment of the superabsorbent particles. In a particular heat-treatment, the formed absorbent composite can be subjected to a temperature of 100° C. for a time period of 5 minutes. In another desired treatment, the formed absorbent composite can be subjected to a temperature of 70° C. for 60 minutes. The absorbent composite is stretchable, and more particularly, can be elastomerically stretchable. In a particular feature, the absorbent composite can have a stretchability value of at least about 30%. In particular aspects, the stretchability value can be at least a minimum of about 50%. The stretchability value can alternatively be at least about 60%, and can optionally be at least about 75% to provide improved benefits. In other aspects, the stretchability value can be up to a maximum of about 300%, or more. The stretchability value can alternatively be up to about 200%, and can optionally be up to about 100% to provide desired effectiveness.

If the stretchability parameter is outside the desired values, composite may not be sufficiently flexible to provide desired levels of fit and conformance to the shape of the user. A donning of a product that includes the composite 30 can be more difficult. For example, training pant products may be accidentally stretched to large amounts before use, and the absorbent system may rip and tear. As a result, the absorbent composite may exhibit excessive leakage problems.

The stretchability of an overall layer or other component can be determined by employing the Composite Stretchability Test, which is described in the TEST METHODS section of the present disclosure. In a desired feature, the selected, desired stretchability value can be achieved with an applied stretching force of 150 grams-force (gmf) per inch of width of the test specimen (0.58 N/cm)

Another feature of the invention can include superabsorbent particles which have been combined with the elastomeric polymer fibers during a formation of the polymer fibers, and the formation of the polymer fibers has included a meltblowing operation. Where the absorbent composite 30 includes cellulosic fibers, the superabsorbent particles can be operatively mixed with the cellulosic fibers, and the mixture can then be operatively combined with the meltblown polymer fibers.

The stretchable absorbent composite can provide an improved holding and retention of the superabsorbent particles in the matrix of elastomeric fibers. In a particular aspect, the absorbent composite 30 can be configured to provide a superabsorbent shake-out value of not more than a maximum of about 2%. The provided shake-out value can alternatively be not more than about 1.2%, and can optionally be not more than about 1% to provide improved benefits. In further features, the shake-out value can be not more than about 0.8% or not more than about 0.5% to provide further improved benefits. A suitable technique for determining the superabsorbent shake-out value of an absorbent composite can employ the Shake-Out Test, which is described in the TEST METHODS section of the present disclosure.

Techniques and systems for producing nonwoven fibrous webs which include meltblown fibers are well known in the art. For example, a suitable technique is disclosed in U.S. Pat. No. 4,100,324 to R. A. Anderson. Other suitable techniques are described in U.S. Pat. No. 5,350,624 to W. A. Georger, and U.S. Pat. No. 5,508,102 to W. A. Georger. Absorbent, elastomeric meltblown webs containing high amounts of superabsorbent are described in U.S. Pat. No. 6,362,389, to D. J. McDowall. The entire disclosures of these documents are incorporated herein by reference in a manner that is consistent herewith. The meltblowing techniques can be readily adjusted in accordance with conventional know-how to provide turbulent flows that can operatively mix the selected fibers and superabsorbent particles. In a desired arrangement, the particles and selected fibers can be substantially homogeneously mixed during the process of forming a web of the stretchable absorbent composite material. The techniques can also be readily adjusted in accordance with conventional knowledge to provide the desired weight percentages of the selected fibers and superabsorbent particles.

Figure 4:
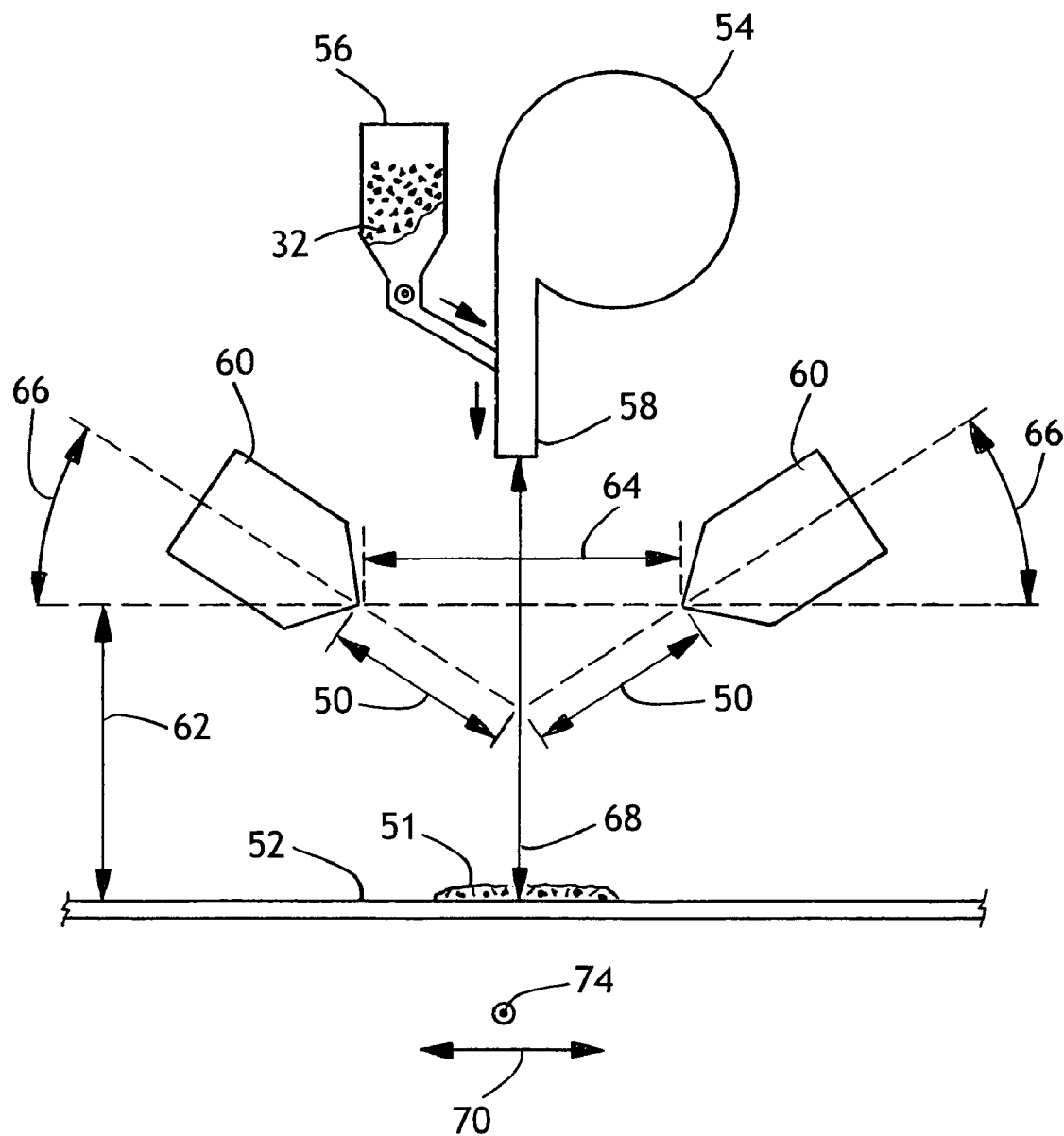
FIG. 4 shows a representative process and apparatus for producing an elastomeric, absorbent composite web.

With reference to FIG. 4, a meltblowing process and apparatus for forming a stretchable, absorbent composite web 51 can have an appointed machine-direction 74 which extends longitudinally along the processing sequence of the process and apparatus, and an appointed lateral cross-deckle direction 70 which extends transversely. For the purposes of the present disclosure, the machine-direction is the direction along which a particular component or material is transported length-wise along and through a particular, local position of the apparatus and process. The cross-deckle direction 70 can lie generally within the plane of the material being transported through the method and apparatus, and is aligned perpendicular to the local machine-direction. Accordingly, with reference to the arrangement representatively shown in FIG. 4, the machine-direction 74 extends perpendicular to the plane of the sheet of the drawing. As representatively shown, the process and apparatus can include a conventional fiberizer 54 which, if desired, provides the desired amount of cellulosic fibers; an operative supply 56 of superabsorbent particles 32; and a delivery chute 58 which directs the superabsorbent particles and cellulosic fibers, if any, into the cooperating portions of the forming process. The superabsorbent supply system 56 can include any conventional metering device for providing a desired, flow rate of particles into the process. The forming process can further include a system of meltblowing dies 60 which provide the desired elastomeric polymer fibers, and a foraminous forming surface 52 on which a composite web can be formed. The forming surface can, for example, be provided by a forming belt or by the generally cylindrical, peripheral surface of a rotatable forming drum. The composite web 51 can be formed in a substantially continuous operation, and the web can include the superabsorbent particles operatively held in contained in the matrix of elastomeric polymer fibers 34, as well as any incorporated cellulosic fibers.

In particular configurations, selected processing parameters can be appropriately controlled to produce desired characteristics in the stretchable absorbent composite 30. For example:

Melt-temperature—Higher melt-temperatures can provide better containment of the incorporated particles (less shake-out). The elastomeric polymer can stay molten longer, thereby increasing the chance that the particles will hit and attach to molten/softened polymer.

Die-to-Die Width—This parameter is the distance 64 representatively shown in FIG. 4. A smaller die-to-die width 64 can give higher containment of the incorporated particles. The meltblown polymer fibers travel a smaller distance before contacting the superabsorbent particles, and the particles can more readily connect to and be captured by the still soft and sticky polymer material. The die-to-die width distance 64 can, for example, be within the range of about 11.4-17.8 cm (about 4.5-7 inch). In a desired configuration, the die-to-die width can be about 14 cm (about 5.5 inch).

Relative Humidity—Lower relative humidity can provide a higher containment of the incorporated particles. Ambient, liquid moisture can hinder the attachment between the particles and the polymer fibers. The particles may preferentially attach to the liquid instead of the polymer.

External Surfactant—Lower amounts of externally-applied (e.g. sprayed-on) surfactant can provide a higher containment of particles. The liquid surfactant can hinder the attachment between the particles and the polymer fibers. The particles may preferentially attach to the liquid instead of the polymer.

Vacuum—This parameter is the vacuum level (e.g. measured in inches of water) that is generated under the foraminous forming surface and the composite web during the web forming operation. A higher vacuum can provide a higher containment of particles. The higher vacuum can help provide a tighter, more locked-together structure.

Fiber Diameter/Primary air pressure—This parameter is the air pressure of the forming gas (e.g. air) that is generated close to the exit of the air channels that are typically incorporated at the tip of the meltblowing die 60 The primary air pressure can, for example be expressed in the units of "psig" (pounds per square inch—gauge). For example, a selected exit air velocity, typically in the range of 0.4-1.0 Mach can be provided at the air exit, depending on the primary air pressure and the air gap spacing employed within the meltblowing die. The air gap spacing is measured from a knife edge of the meltblowing die tip to an inside edge of the air plate in the meltblowing die. In a typical arrangement, the air gap spacing can be within the range of about 0.015-0.084 inch. A higher, primary-air pressure can create smaller fibers and help provide a higher containment of the particles. The smaller fibers can provide an increased amount of surface area to which the particles can attach. The smaller fibers are also more flexible and can more readily entangle around a superabsorbent particle.

Die angle—This parameter is the angle 66 representatively shown in FIG. 4. A large angle from the horizontal can reduce contact between the polymer fibers and the particles. The reduced contact can decrease the containment of the particles in the composite, and can also create a non homogenous (layered) sheet which can degrade the containment of the superabsorbent particles. The die angle 66 can, for example be within the range of about 35°-65° from horizontal. In a particular arrangement, the die angle can be about 45° from horizontal.

Forming Height (Die-to-table)—This parameter is the distance 62 between the meltblowing die 60 and the forming surface 52. A lower forming height can provide a higher containment of particles. Fiber entanglements can form more quickly and can help hold and secure the particles in the composite web. The forming height 62 can, for example, be within the range of about 25.4-40.6 cm (about 10-16 inch). Particular arrangements can incorporate a forming height of about 33 cm (about 13 inch).

Chute Height (Chute to table)—This parameter is the minimum distance 68 between the exit of the delivery chute 58 and the forming surface 52. A lower chute height 68 may give higher containment of the particles, as long as the particles are sufficiently attached to the polymer fibers before hitting the table. It is believed that the velocity of the particles can shoot the particles straight down the middle region of the system of meltblowing dies employed to form the elastomeric polymer fibers, and can quickly move the particles into the molten polymer. When the fibers and particles hit the table. The chute height 68 can, for example, be within the range of about 25.4-46 cm (about 10-18 inch). Particular arrangements of the process and apparatus can include a chute height of about 41.3 cm (about 16.25 inch).

Additionally, the configuration of the process and apparatus can provide a slant distance 50. Particular aspects of the process and apparatus can be configured to provide a slant distance within the range of about 4-6 inch (about 10-16.3 cm). In a desired arrangement, the slant distance can be about 5 inch (about 13 cm) to provide desired benefits.

The process and apparatus can also be arranged to provide a selected chute angle. In the various configurations of the invention, the outlet opening of the delivery chute 58 can have a short-axis and a long-axis. As representatively shown in FIG. 4, the short axis can extend generally along the cross-deckle direction 70 and the long-axis can extend generally perpendicular to the plane of the drawing sheet. The chute angle is the angle between the long-axis of the delivery chute and the local machine-direction. A chute angle of zero degrees can, for example, have the long-axis of the delivery chute 58 aligned along the machine-direction of the process and apparatus. Additionally, the long-axis can be approximately centered along the cross-deckle direction 70 of the forming surface. A chute angle of 20 degrees can have the long-axis of the delivery chute rotated 20 degrees away from the local machine-direction at the position of the delivery chute. would have the delivery chute. The long-axis of the delivery chute can also be substantially centered along the cross-deckle direction of the forming surface. In particular aspects, the chute angle can be within the range of about 0°-90°. Desired arrangements of the process and apparatus can include a chute angle of about 20° to provide desired performance.

A further feature of the invention can include an elastomeric, absorbent composite 30 which has been subjected to a distinctive curing operation after the formation of the composite web material. The curing operation can include a distinctive curing time, and can further include a distinctive curing temperature. In a particular aspect, the curing time can be at least a minimum of about 5 minutes. The curing time can alternatively be at least about 10 minutes, and can optionally be at least about 30 minutes to provide desired benefits. In other aspects, the curing time can be up to a maximum of about 75 minutes, or more. The curing time can alternatively be up to about 70 minutes, and can optionally be up to about 60 minutes to provide desired effectiveness.

In another aspect, the absorbent composite 30 can be subjected to a curing temperature which is at least a minimum of about 60° C. The curing temperature can alternatively be at least about 70° C., and can optionally be at least about 80° C. to provide improved performance. In other aspects, the curing temperature can be up to a maximum of about 130° C., or more. The curing temperature can alternatively be up to about 120° C., and can optionally be up to about 100° C. to provide improved effectiveness.

If the curing time and/or curing temperature are outside the desired values, the superabsorbent particle may not be sufficiently bonded to the fibers in the absorbent composite, and the absorbent composite can exhibit excessive levels of particle shake-out. In other effects, the absorbent composite may exhibit an insufficient level of stretchability.

The absorbent composite 30 can have a selected density, as determined under a confining pressure of 0.05 psi (0.345 KPa). In a particular feature, the absorbent composite density can be at least a minimum of about 0.1 grams per cubic centimeter ($g/cm^3$). The density of the absorbent composite can alternatively be at least about 0.25 $g/cm^3$, and can optionally be at least about 0.3 $g/cm^3$. In another feature the absorbent composite density can be up to about 0.4 $g/cm^3$. The sample density can affect the shake-out value of the absorbent composite. A higher density can be helpful to decrease the superabsorbent shake-out from the absorbent composite. Desired configurations of the stretchable absorbent composite can have a density within the range of about 0.20 to 0.35 $g/cm^3$.

As previously mentioned, the article 20 may further include a backsheet, and a liquid-permeable topsheet. Additionally, the absorbent composite 30, which includes the matrix of elastomeric polymer fibers and the superabsorbent particles, can be operatively sandwiched between the topsheet and backsheet.

The bodyside liner or topsheet 26 that may be included in the article 30 can include a layer constructed of any operative material, and may be a composite material. For example, the topsheet layer can include a woven fabric, a nonwoven fabric, a polymer film, a film-fabric laminate or the like, as well as combinations thereof. Examples of a nonwoven fabric include spunbond fabric, meltblown fabric, coform fabric, a carded web, a bonded-carded-web, a bicomponent spunbond fabric or the like as well as combinations thereof. Other examples of suitable materials for constructing the topsheet layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof. In desired arrangements, the topsheet layer can be configured to be operatively liquid-permeable.

A more particular example of a suitable topsheet layer material can include a bonded-carded-web composed of polypropylene and polyethylene, such as has been employed as a topsheet stock for KOTEX brand pantiliners, and has been obtainable from Vliesstoffwerk Christian Heinrich Sandier GmbH & Co. KG, a business having an address at Postfach 1144, D95120 Schwarzenbach/Saale, Germany. Other examples of suitable materials are composite materials of a polymer and a nonwoven fabric material. The composite materials are typically in the form of integral sheets generally formed by the extrusion of a polymer onto a web of spunbond material. In a desired arrangement, the topsheet layer 26 can be configured to be operatively liquid-permeable with regard to the liquids that the article is intended to absorb or otherwise handle. The operative liquid-permeability may, for example be provided by a plurality of pores, perforations, apertures or other openings, as well as combinations thereof, that are present or formed in the topsheet layer. The apertures or other openings can help increase the rate at which bodily liquids can move through the thickness of the topsheet layer and penetrate into the other components of the article (e.g. into the absorbent structure 30). The selected arrangement of liquid-permeability is desirably present at least on an operative portion of the topsheet layer that is appointed for placement on the body-side of the article. The topsheet layer 26 can provide comfort and conformability, and can function to direct bodily exudates away from the body and toward the absorbent structure 30. In a desired feature, the topsheet layer 26 can be configured to retain little or no liquid in its structure, and can be configured to provide a relatively comfortable and non-irritating surface next to the body-tissues of a female wearer. The topsheet layer 26 can be constructed of any material which is also easily penetrated by bodily fluids that contact the surface of the topsheet layer.

The topsheet 26 can also have at least a portion of its bodyside surface treated with a surfactant and/or a menses modifier to increase the surface energy of the material surface or reduce the viscoelastic properties of the menses, and to render the topsheet more hydrophilic and more wettable to body fluids. The surfactant can permit arriving bodily liquids to more readily penetrate the topsheet layer. The surfactant may also diminish the likelihood that the arriving bodily fluids, such as menstrual fluid, will flow off the topsheet layer rather than penetrate through the topsheet layer into other components of the article (e.g. into the absorbent body structure). In a particular configuration, the surfactant can be substantially evenly distributed across at least a portion of the upper, bodyside surface of the topsheet 26 that overlays the upper, bodyside surface of the absorbent.

The topsheet 26 may be maintained in secured relation with the absorbent structure 30 by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the absorbent with portions of the adjacent surface of the topsheet, or fusing at least portions of the adjacent surface of the topsheet to portions of the adjacent surface of the absorbent.

The topsheet 26 typically extends over the upper, bodyside surface of the absorbent structure, but can alternatively extend around the article to partially or entirely, surround or enclose the absorbent structure. Alternatively, the topsheet 26 and the backsheet 28 can have peripheral margins which extend outwardly beyond the terminal, peripheral edges of the absorbent structure 30, and the extending margins can be joined together to partially or entirely, surround or enclose the absorbent structure.

The backsheet 28 that may be included in the article can include a layer constructed of any operative material, and may or may not have a selected level of liquid-permeability or liquid-impermeability, as desired. In a particular configuration, the baffle or backsheet 28 may be configured to provide an operatively liquid-impermeable backsheet structure. The backsheet may, for example, include a polymeric film, a woven fabric, a nonwoven fabric or the like, as well as combinations or composites thereof. For example, the backsheet may include a polymer film laminated to a woven or nonwoven fabric. In a particular feature, the polymer film can be composed of polyethylene, polypropylene, polyester or the like, as well as combinations thereof. Additionally, the polymer film may be micro-embossed. Desirably, the backsheet 28 can operatively permit a sufficient passage of air and moisture vapor out of the article, particularly out of an absorbent (e.g. storage or absorbent structure 30) while blocking the passage of bodily liquids. An example of a suitable backsheet material can include a breathable, microporous film, such as a HANJIN Breathable Backsheet available from Hanjin Printing, Hanjin P&C Company Limited, a business having offices located in Sahvon-li.Jungan-mvu.Kongiu-City, Chung cheong nam-do, Republic of South Korea. The backsheet material is a breathable film, which is dimple embossed and contains: 47.78% calcium carbonate, 2.22% $TiO_2$, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable backsheet material can include a closed cell polyolefin foam. For example, closed cell polyethylene foam may be employed. Still another example of a backsheet material would be a material that is similar to a polyethylene film which is used on commercially sold KOTEX brand pantiliners, and is obtainable from Pliant Corporation, a business having offices located in Schaumburg, Ill., USA.

The absorbent body structure that is included in the article can be operatively configured to provide desired levels of absorbency and storage capacity, and desired levels of liquid acquisition and distribution. More particularly, the absorbent body can be configured to hold a liquid, such as urine, menses, other complex liquid or the like, as well as combinations thereof. As representatively shown, the absorbent body can include a matrix of absorbent fibers and/or absorbent particulate material, and the absorbent fiber can include natural and/or synthetic fiber. The absorbent body may also include one or more components that can modify menses or inter-menstrual liquids.

In desired configurations, the elastomeric absorbent composite 30 can provide a specific retention capacity and a total retention capacity. The specific retention capacity of an overall layer or other component can be determined by employing the Centrifuge Retention Capacity Test, which is described in the TEST METHODS section of the present disclosure. The total absorbent retention capacity of an overall layer or other component can be determined by multiplying its specific saturation capacity times the total weight of such component.

In optional arrangements, a selected configuration of garment adhesive, such as one or more strip regions, may be distributed onto the garment-side of the article to help secure the article to a wearer's undergarment. Typically, the garment adhesive is distributed over the garment-side of the backsheet, and one or more layers or sheets of release material can be removably placed over the garment adhesive to top-sheet the adhesive for storage prior to use.

The article 20 can include a system of side-panels 42, which can provide desired "ear" or "wing" portions, depending on the desired configuration of the article. The side-panels can be unitarily formed from a selected component of the article, such as the topsheet and/or the backsheet, and are integrally connected to appointed sections of the side regions along a selected portion of the article. In adult or infant incontinence products, for example, the side-panels may be joined to extend laterally from the longitudinal end regions of an individual product, and may be configured to operatively encircle a wearer's waist. In feminine care products, the side-panels may be joined to extend laterally from the intermediate portion 76 of the article, and may be configured to be operatively wrapped and secured around the side edges of a wearer's undergarment to help hold the article in place. Alternatively, the side-panels or wings can be separately provided members that are subsequently attached or otherwise operatively joined to the appointed portion of the article 20.

The side-panel portions 42 can have any operative construction, and can include a layer of any operative material. Additionally, each side-panel can comprise a composite material. For example, the side-panels may include a spunbond fabric material, a bi-component spunbond material, a necked spunbond material, a neck-stretched-bonded-laminate (NBL) material, a meltblown fabric material, a bonded carded web, a thermal bonded carded web, a through-air bonded carded web or the like, as well as combinations thereof.

Each side-panel 42 can be joined to its corresponding side region of the article in any operative manner. For example, the side-panel can be joined to the topsheet 26, the backsheet 28 or another article component, as well as any combination thereof. In the illustrated example, each side-panel 42 is joined to the outward, garment-side surface of the backsheet 28, but may optionally be joined to the bodyside surface of the backsheet. The side-panel can be attached with hotmelt adhesive, but any other operative adhesive or attachment mechanism may alternatively be employed.

In another feature, each side-panel portion 42, or any desired combination of the employed side-panel portions, can include a panel-fastener component which is cooperatively joined to an appointed, landing zone or engagement surface of the article. The panel-fastener can include a system of interengaging mechanical fasteners, a system of adhesive fasteners or the like, as well as combinations thereof.

Each side-panel 42 can, for example, include a loop or other "female" component of an interengaging mechanical fastener system. Alternatively, each side-panel can include a hook or other "male" component of the mechanical fastener system. Any operative hook component may be employed. For example, a suitable hook component materials can include a J-hook, mushroom-head hook, flat-top nail-head hook, a palm-tree hook, a multiple-J hook or the like, as well as combinations thereof. Alternatively, either or both side-panels 42 can include a panel-fastener system which incorporates an operative adhesive. The adhesive may be a solvent-base adhesive, a hotmelt adhesive, a pressure-sensitive adhesive, or the like, as well as combinations thereof.

In the various arrangements of the present invention, the hook component can be configured to have a particularly selected hook concentration or density (hooks per unit area).

In a particular aspect, the hook density can be at least a minimum of about 1500 hooks/in$^2$ (about 232 hooks/cm$^2$). The hook density can alternatively be at least about 2000 hooks/in$^2$ (about 310 hooks/cm$^2$), and can optionally be at least about 3000 hooks/in$^2$ (about 465 hooks/cm$^2$) to provide improved performance. In another aspect, the hook density can be not more than a maximum of about 7000 hooks/in$^2$ (about 1085 hooks/cm$^2$). The hook density can alternatively be not more than about 6000 hooks/in$^2$ (about 930 hooks/cm$^2$), and can optionally be not more than about 5000 hooks/in$^2$ (about 775 hooks/cm$^2$) to provide improved performance.

Examples of suitable hook materials can include 85-Series and 61-Series hook materials available from Velcro, U.S.A., a business having offices located in Manchester, N.H., U.S.A. The hook materials can have a hook density of about 775 hooks/cm$^2$.

In particular arrangements, the material of the loop component may include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515 entitled PATTERN-UNBONDED NONWOVEN WEB AND PROCESS FOR MAKING THE SAME, by T. J. Stokes et al., and granted Jan. 12, 1999; the entire disclosure of which is incorporated herein by reference in a manner that is consistent herewith.

In the construction of the article 20, the various components may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

Test Methods

Composite Stretchability Test

To determine the stretchability of a material, a predetermined amount of elongation is chosen: e.g. 30%, 50%, 100% etc. The amount of stretch provides a corresponding stretch ratio: e.g. 130%, 150% 200% etc. For each level of stretchability testing, three specimens are tested and all three must pass in order to consider the sample as having the respective level of stretchability. A sufficient amount of stretching force is applied to the specimen, as needed to generate the selected amount of stretching. Each specimen is tested only once, even if the specimen is not damaged.

The stretchability of a composite is measured after 3 cycles with each cycle including (a) stretching to a predetermined ratio of extension, and (b) releasing the stretching force, thereby allowing the stretched composite to retract back towards its original dimension.

Stretchability is defined according to the following equation:

$$\text{Stretchability} = (L_e - L_o) \times 100\% / L_o$$

wherein $L_e$ is the length after extension (i.e., at the predetermined ratio), and $L_o$ is the original sample length. For a sample to be qualified as having a predetermined stretchability, the sample must be able to demonstrate all of the following requirements:

(1) The sample must be able to reach the predetermined stretch ratio.

(2) The sample must be able to retract at least 70% of the extension within a 1-minute interval after the applied stretching force is removed, as measured in the third stretching cycle. The percent retraction is defined as:

$$\text{Retraction (\%)} = \{1 - (L_f - L_o)/(L_e - L_o)\} \times 100\%$$

wherein $L_f$ is the sample length after the force has been released for 1-minute, $L_e$ is the length after extension (i.e., the predetermined ratio), and $L_o$ is the original sample length before extension.

(3) The sample must meet the first criterion after the first and second extension, and meet the second criterion after the third extension on the same specimen. (In carrying out the test, the retraction criterion is measured only after the third extension).

Desirably, the sample exhibits no visible structural defects, such as excessive voids or cracks, after the stretchability testing.

The absorbent composite was cut into 3-inch (7.62 cm) by 7-inch (17.78 cm) specimens. An INSTRON 4443, available from Instron Corporation of Canton, Mass., was used to measure stretchability. A substantially equivalent testing device may optionally be employed. Each specimen was mounted onto the equipment vertically with two clamps and the locations of the clamps were marked on the specimen. The distance between the two clamps ($L_o$) was 4 inches (10.16 cm). The specimen was stretched by moving the upper clamp upward at a rate of 500 mm/min and held for 5 seconds at the predetermined length of extension ($L_e$). After 5 seconds of holding, the upper clamp was returned to the original position and the specimen was free to retract. The second cycle of stretching was started after the upper clamp was back in the original position for 10 seconds, followed by the third cycle. The stretching and retraction procedure for the second and third cycles was the same as the first cycle. The specimen was removed from the equipment after completion of the third stretching cycle and laid on the bench. The distance between the two marks ($L_f$) was measured after the specimen was relaxed for 1 minute. For each absorbent composite, test specimens were prepared and subjected to stretchability testing with respect to both the machine direction (MD) and the cross-machine direction (CD) of the absorbent composite. The lower stretchability value measured from the CD and MD directions was chosen to represent stretchability of the absorbent composite.

Shake-Out Test

A suitable apparatus and procedure for determining the shake-out value of a sample material is described in PCT publication WO 02/076520 entitled HIGH SUPERABSORBENT CONTENT WEBS AND A METHOD FOR MAKING THEM published Oct. 3, 2002. The entire disclosure of this document is incorporated herein by reference.

The susceptibility of a superabsorbent/fiber web to the migration and escape of superabsorbent material (SAM) can be measured by employing a Shakeout Test procedure which involves agitating web samples in a controlled fashion and determining the total loss of web mass from the sample. A sample of the stretchable absorbent composite is prepared in the shape of a rectangular plate which has a length of 9 inch (22.86 cm) and a width of 4 inch (10.16 cm). The sample has the density that would be present when the absorbent composite is incorporated in its intended end-product article. Any tissues or other layers that were employed during the process of airforming the sample materials are removed from all specimens before conducting the Shakeout Test.

The Shakeout Test can be conducted by employing a Model # RX-24 PORTABLE SIEVE SHAKER (herein after referred to as "RX-24") available from W. S. Tyler Inc., a business having offices located in Mentor, Ohio, U.S.A. The shaker apparatus is modified in the manner described in PCT publication WO 02/076520, which corresponds to U.S. patent application Publication 2002/0183703 A1. The entire disclosure of this document is incorporated herein by reference in a manner that is consistent herewith. For use in the Shakeout Tests, the RX-24 is modified to shake web samples and allow a determination of the web's resistance to the migration of superabsorbent material (SAM), based on the mass of web material lost during the shaking. The modifications to the shaker apparatus involve making changes to the guide frame in the manner described in PCT publication WO 02/076520. In addition to the changes to the guide frame described in this PCT publication, a modified sample holder was employed in the shakeout test. The sample holder had a frame made of polyacrylate plate and two pieces of mesh screen. The frame had a length of 17 inch (43.18 cm), a width of 11.5 inch (29.21 cm) and a thickness of 0.20 inch (0.51 cm). The frame had a rectangular opening with a length of 15.25 inch (38.74 cm) and a width of 6.25 inch (15.88 cm), and the opening was substantially centered in the frame. One piece of mesh screen with a dimension slightly larger than the opening was operatively joined on each side of the frame (e.g. with duct tape) to hold the test sample. The mesh screen had 0.4 cm×0.4 cm square openings, and the total weight of the sample holder was about 500 grams. A substantially equivalent shaker system may optionally be employed.

To perform the Shakeout Test, the absorbent composite sample is laid at the center of the sample holder, and the sample holder is laid horizontally flat (i.e. parallel to the floor) upon the wire screen employed to support the sample on the modified RX-24. The RX-24 then shakes the web at a frequency of approximately 520 cycles per minute for a period of five minutes. If any sheets of tissue paper or other material have been placed above or below the sample to facilitate the lifting or handling of the web samples, those sheets are removed prior to shaking.

After the completion of the shaking portion of the test, the mass loss and the superabsorbent-loss are determined by comparing the total remaining mass of the absorbent composite sample with the original mass of the sample when the sample was initially placed on the support screen, in accordance with the following formula:

Mass loss (%)=100%×(($M_0-M_{end}$)÷$M_0$)

where: $M_0$=sample mass prior to shakeout test (e.g. grams);

$M_{end}$=sample mass remaining after test (e.g. grams).

Mass that is lost from the sample will generally fall through the openings in the support screen. Any mass that remains on the screen is counted as mass loss. The shake-out value (%) is the total mass loss (%) produced at the above-described shaking conditions.

While the foregoing discussion has described in detail one desirable method for conducting the Shakeout test using a specific type of apparatus, it will be appreciated that those skilled in the art will be able to prepare other apparatus that will allow equivalent testing in which agitation applied to webs will yield the identical results in terms of web loss as that achieved by the disclosed Shakeout Test. Accordingly, the scope of the Shakeout Test will include any equivalent test methods for determining web loss.

Centrifuge Retention Capacity (CRC) Test

The Centrifuge Retention Capacity (CRC) Test measures the ability of the superabsorbent material to retain liquid therein after being saturated and subjected to centrifugation under controlled conditions. The resultant retention capacity is stated as grams of liquid retained per gram weight of the sample (g/g). The sample to be tested is prepared from particles which are prescreened through a U.S. standard 30 mesh screen and retained on a U.S. standard 50 mesh screen. As a result, the sample comprises particles sized in the range of about 300 to about 600 microns (micrometers). The particles can be prescreened by hand or automatically and are stored in a sealed airtight container until testing.

The retention capacity is measured by placing 0.2±0.005 grams of the prescreened sample into a water-permeable bag which will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat-sealable filter paper works well for most applications. The bag is formed by folding a 12.7 cm by 7.62 cm (5-inch by 3-inch) sample of the bag material in half and heat-sealing two of the open edges to form a 6.35 cm by 7.62 cm (2.5-inch by 3-inch) rectangular pouch. The heat seals should be about 0.635 cm (0.25 inches) inside the edge of the material. After the sample is placed in the pouch, the remaining open edge of the pouch is also heat-sealed. Empty bags are also made to serve as controls. Three samples (e.g., filled and sealed bags) are prepared for the test. The filled bags must be tested within three minutes of preparation unless immediately placed in a sealed container, in which case the filled bags must be tested within thirty minutes of preparation.

The bags are placed between two, polytetrafluoroethylene (e.g. TEFLON material) coated fiberglass screens having 7.62 cm (3 inch) openings (available from Taconic Plastics, Inc., a business having offices located in Petersburg, N.Y., U.S.A.) and submerged in a pan of the test solution at 23 degrees Celsius, making sure that the screens are held down until the bags are completely wetted. After welting, the samples remain in the solution, for about 30±1 minutes, at which time they are removed from the solution and temporarily laid on a non-absorbent flat surface. For multiple tests, the pan should be emptied and refilled with fresh test solution after 24 bags have been saturated in the pan.

The wet bags are then placed into the basket of a suitable centrifuge capable of subjecting the samples to a g-force of about 350. A suitable centrifuge is a HERAEUS LABOFUGE 400 having a water collection basket, a digital rpm gauge, and a machined drainage basket adapted to hold and drain the bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the samples. The amount of solution retained by the sample, taking into account the solution retained by the bag itself, is the specific, centrifuge retention capacity (CRC) of the sample, expressed as grams of retained liquid per gram of sample. More particularly, the specific retention capacity is determined in accordance with the following formula:

$$\frac{\text{(Sample \& bag weight after centrifuge)} - \text{(empty bag weight after centrifuge)} - \text{(dry sample weight)}}{\text{dry sample weight}}$$

The three samples are tested and the results are averaged to determine the retention capacity (CRC) of the superabsorbent material. The samples are tested at 23±1 degrees Celsius and 50±2 percent relative humidity.

Thermal Stickiness Index (TSI) Test

The superabsorbent particles before the test were pre-screened to have a particle size range from 300 microns to 600 microns. Five grams of the screened superabsorbent particles were weighed and added into a 100 ml PYREX glass beaker. The beaker was gently shaken to form a uniform layer of the superabsorbent sample on the bottom of the beaker. The beaker was then placed in a convectional oven at 150° C. for 10 minutes. The beaker was taken out of the oven and cooled at room temperature for at least 15 minutes until the temperature of the beaker was back to room temperature. Turn the cooled beaker up side down and collect all the superabsorbent particles that falls out of the beaker. Weights of the original amount of superabsorbent in the beaker and the amount of superabsorbent fallen out of the beaker were used to determine the thermal stickiness index (TSI), in accordance with the following formula:

$$TSI = \frac{W_{original} - W_{fallen}}{W_{original}} \times 100$$

The following Examples describe particular configurations of the invention, and are presented to provide a more detailed understanding of the invention. The Examples are not intended to limit the scope of the present invention in any way. From a complete consideration of the entire disclosure, other arrangements within the scope of the claims will be readily apparent to one skilled in the art.

EXAMPLES

Superabsorbent particles with thermally processible, water soluble polymer coatings have been prepared in accordance with the following.

A first, Coating Polymer 1 solution included a first combination of two monomer solutions 1A and 1B, which were prepared separately:

Solution No. 1A was prepared as follows: 22.0 grams of a 75% solution of (3-acrylamidopropyl)trimethyl ammonium chloride (0.08 moles) were added to 70 grams of deionized water, followed by 43 grams of hydroxyethyl methacrylate (0.32 mol) and 12 grams of PEG 200 (molecular weight 200). Then, 0.36 grams ($1.02 \times 10^{-3}$ moles) of ascorbic acid were added to the solution. This mixture was stirred with a magnetic stir bar at about 60 rpm in a bath of water at about 23° C. until the ascorbic acid was dissolved and the mixture cooled to 23° C.

Solution No. 1B was prepared in the following manner: 22.0 grams of a 75% solution of (3-acrylamidopropyl)trimethyl ammonium chloride (0.08 moles) were added to 70 grams of deionized water, followed by 43 grams of hydroxyethyl methacrylate (0.32 mol) and 12 grams of PEG 200 (molecular weight 200). Then 0.74 grams of 30% aqueous hydrogen peroxide were added. This mixture was stirred with a magnetic stir bar at about 60 rpm in a bath of water at about 23° C. to provide a clear solution cooled to 23° C.

Solution No. 1B was added to Solution No. 1A while stirring with a magnetic stir bar. A thermocouple was used to monitor the temperature and observe the reaction exotherm. No polymerization exotherm was evident so the mixture was placed into a water bath and the temperature was raised to 70° C. over a time period of 35 minutes. An exotherm was evidenced by a rise in temperature to 74° C. over a period of 1 minute, and the solution became highly viscous. The reaction beaker was removed from the water bath after 90 minutes from the time that Solution No. 1B was added to Solution No. 1A. 300 grams of deionized water were added to reduce the polymer concentration to about 26%.

A second, Coating Polymer 2 solution included a second combination of two monomer solutions 2A and 2B which were prepared separately:

Solution No. 2A was prepared as follows: 73.2 grams (1.016 moles) of acrylic acid were added to 12 grams polyethylene glycol (mol. wt.=200) and 16.3 grams of sodium hydroxide in 100 grams of water (40% neutralization), and 0.5 grams of ascorbic acid. This solution was cooled in an ice bath following dissolution of the ascorbic acid.

Solution No. 2B was prepared as follows: 28.8 grams of a 75% solution of (3-acrylamidopropyl)trimethyl ammonium chloride (0.10 moles) were added to 100 grams of deionized water followed by 12 grams of PEG 200 (molecular weight 200). To this solution were added 1.04 g of 30% aqueous hydrogen peroxide.

Solution No. 2B was added to Solution No. 2A in an ice bath while stirring with a magnetic stir bar. A thermocouple was used to monitor the temperature and observe the reaction exotherm. The polymerization reaction began after about 5 minutes of mixing. Once the exotherm reaction was detected, water was added gradually to keep the solution viscosity suitable for stirring. A total of 300 gram of water was added over 20 minutes. A maximum polymerization temperature of 65° C. was observed about 8 minutes after the mixing of the two monomer solutions 2A and 2B. The polymer concentration was found, by evaporation of the water to be about 22%.

Quantities of superabsorbent particles were coated with Coating polymer 1 and other quantities of superabsorbent particles were coated with Coating polymer 2. For the coating each quantity of coated superabsorbent particles, the following procedure was employed.

Each employed solution of Coating polymer was diluted to 6.67% with distilled water. 750 grams of the selected polymer solution was added to the mixing bowl of a HOBART Mixer, model N-50, available from Hobart Canada, North York, Ontario, Canada. With the solution agitated at a speed setting of "3", 500 grams of superabsorbent was added. The mixture became a fluffy mass of slightly swollen superabsorbent. The swollen superabsorbent was dried for 3 days at 80° C. and then de-agglomerated with a GRANU-GRINDER, available from C. W. Brabender, a business having offices located in Hackensack, N.J., U.S.A. The particles were then sieved to remove particles larger than 850 microns.

The samples in Tables 1, 2 and 3 were made under the same process conditions, except that there were some variations in the employed Primary Air Temperature (PAT). The samples in Tables 1 and 3 were made with a PAT about 280° C. In Table 2, with the different elastic polymers, the primary air temperature varied, and had the values set forth in Table 2. With the samples in Tables 1, 2 and 3, the Elastic polymer-Superabsorbent-Pulp weight ratios were 15:75:10, and for all of the samples, the basis weight was 425 grams per square meter (g/m$^2$). The pulp employed in the samples was SULPHATATE HJ woodpulp, commercially available from Rayonier Inc., a business having offices located at Jesup, Ga., USA. The elastomeric polymer employed in the samples of Tables 1 and 3 was KRATON G2755 elastomer, which is available from Kraton Inc. of Houston, Tex., U.S.A. The superabsorbents SXM 9543, SXM 9394 and FAVOR 880, are all available from Degussa Superabsorber Inc., a business having offices located at Greensboro, N.C., U.S.A. The Bipolar superabsorbent E1239-11 is available from BASF Inc., a business having offices located at Portsmouth, Va., U.S.A.

TABLE 1

Composite Shake-Out with Various SAMs

| Sample No. | SAM Types | Shake-out % | Stretchability % |
|---|---|---|---|
| 1 | SXM 9543 | 4.10 | 100 |
| 2 | SXM 9394 | 1.33 | 100 |
| 3 | BASF Bipolar E1231-99 | 1.90 | 100 |
| 4 | FAVOR 880 | 3.38 | 100 |

Note:
All samples in Table 1 contained 75 wt % superabsorbent material, 15 wt % KRATON G2755 elastomeric fiber, and 10 wt % Sulfate-HJ woodpulp.

TABLE 2

Composite Shake-Out with Different Elastic Polymers

| Sample No. | Elastomeric Polymers | Temperature (° C.) Melt-Temp $T_m$ | Temperature (° C.) Primary Air Temp | Shake-out (%) | Stretchability (%) | Vendors |
|---|---|---|---|---|---|---|
| 5 | ESCORENE UL 7710 (EVA) | 138-204 | 140-218 | 4.80 | 50 | ExxonMobil Chemical Company, Houston, Texas, U.S.A. |
| 6 | EXACT (PE) 4023 | 210-263 | 229-279 | 2.51 | 100 | ExxonMobil Chemical Company, Houston, Texas |
| 7 | Boston Compound (80% AFFINITY PE plastomer 8185/ 15% 3 M Tackifier REGLAREZ 1126/5% DOWLEX (WAX) 2503 | 204-232 | 224-252 | 5.58 | 50 | Dow Chemical, Freeport, Michigan, U.S.A. |
| 8 | KRATON G2755 | 249-274 | 279-281 | 1.33 | 100 | Kraton Inc., Houston, Texas |
| 9 | DOW (200 MI) PE plastomer XUS59800.05 | 132-209 | 162-267 | 1.45 | 50 | Dow Chemical, Freeport, Michigan |
| 10 | DOW (500 MI) PE plastomer XUS59800.05 | 151-218 | 177-218 | 10.9 | 50 | Dow Chemical, Freeport, Michigan |
| 11 | PLTD 1723 (Propylene-based developmental elastomer) | 243 | 243-274 | 2.06 | 50 | ExxonMobil Chemical Company, Houston, Texas |

Note:
All samples in Table 2 contained 75 wt % SXM 9394 superabsorbent, 15 wt % elastomeric polymer fiber, and 10 wt % Sulfate-HJ woodpulp.
EVA = ethylene vinyl acetate
PE = polyethylene In Table 3, the superabsorbent materials in samples 13 and 16 were surface treated with Polymer 1. The superabsorbent materials in samples 14 and 17 were surface treated with Polymer 2.

TABLE 3

Composite Shake-Out with the SAM coated by polymer

| Sample No. | Superabsorbent Types | SAM Shake-out (%) Non-cured | *Heat-cured | Stretch-ability (%) |
|---|---|---|---|---|
| 12 | SXM 9543 | 8.55 | 5.67 | 100 |
| 13 | SXM 9543 coated by Polymer 1 | 4.77 | 3.93 | 100 |
| 14 | SXM 9543 coated by Polymer 2 | 2.78 | 1.92 | 100 |
| 15 | SXM 9543 | 8.47 | 5.73 | 100 |
| 16 | SXM 9543 coated by Polymer 1 | 4.80 | 3.19 | 100 |
| 17 | SXM 9543 coated by Polymer 2 | 1.89 | 1.16 | 100 |

Samples 12, 13 and 14 were cured at 100° C. for 5 minutes; samples 15, 16 and 17 were cured at 70° C. for 60 minutes.

A third, Coating Polymer 3 solution included a polyethylene oxide, POLYOX N3000, available from Union Carbide. The coating solution was prepared by dissolving 25 grams of the polyethylene oxide (PEO) in 1,250 grams of distilled water. The dry powder of the POLYOX N3000 was slowly added into the mixing bowl of a HOBART Mixer, model N-50 (available from Hobart Canada, North York, Ontario, Canada) containing the 1,250 grams of distilled water while the mixer was stirred at the stirring setting "1". The solution was stirred until a homogenous solution was obtained. 500 grams of dry superabsorbent particles were then added into the prepared solution while stirring at the above-described stirring setting. The coated, swollen superabsorbent particles were dried at 80° C. until the particles were completely dried. The dried, treated superabsorbent material was de-agglomerated with a GRANU-GRINDER, available from C. W. Brabender, a business having offices located in Hackensack, N.J., U.S.A. The coated superabsorbent particles were then sieved to remove particles larger than 850 microns.

A fourth, Coating Polymer 4 solution included a hydroxypropyl cellulose, KLUCEL GF, available from Hercules Inc. The hydroxypropyl cellulose (HPC) was dissolved into an operative solution. The solution recipe, relative amounts of dry superabsorbent and coating polymer solution, and process of applying the polymer solution and the subsequent processing of the dried, coated superabsorbent material were the same as those employed with the Coating Polymer 3.

A fifth, Coating Polymer 5 solution included a combination of two monomer solutions 5A and 5B which were prepared separately.

Solution No. 5A was prepared as follows: 144 grams (2.0 moles) of acrylic acid were added to 15 grams polyethylene glycol (mol. wt.=8000) and 8.0 grams of sodium hydroxide in 200 grams of water (10% neutralization). Then, 2.0 grams of ascorbic acid were added, and this solution was cooled in an ice bath following the dissolution of the ascorbic acid.

Solution No. 5B was prepared as follows: 144 grams (2.0 moles) of acrylic acid were added to 83 grams polyethylene glycol (mol. wt.=8000) and 8.0 grams of sodium hydroxide in 200 grams of water (10% neutralization). Also added were 4.0 grams of 30% aqueous hydrogen peroxide.

Solution No. 5B was added to Solution No. 5A in an ice bath while stirring with a magnetic stir bar. A thermocouple was used to monitor the temperature and observe the reaction exotherm. The polymerization reaction began after about 5 minutes of mixing. Once the exotherm reaction was detected, water was added gradually to keep the solution viscosity suitable for stirring. A total of 700 gram of water was added over 20 minutes. A maximum polymerization temperature of 75° C. was observed about 10 minutes after the mixing of the two monomer solutions 5A and 5B. After the polymerization was complete a solution of 96 grams (0.2 mole) of diethanol methyl amine in 300 gram of water was added to further neutralize the polymer to 30 mole percent. The polymer concentration was found, by evaporation of the water to be about 22.3%.

A sixth, Coating Polymer 6 solution included a combination of two monomer solutions 6A and 6B which were prepared separately.

Solution No. 6A was prepared as follows: 86.4 grams (1.2 moles) of acrylic acid were added to 43 grams polyethylene glycol (mol. wt.=200) and 14.4 grams of sodium hydroxide in 100 grams of water (30% neutralization). Then, 0.5 grams of ascorbic acid were added, and this solution was cooled in an ice bath following the dissolution of the ascorbic acid.

Solution No. 6B was prepared as follows: 97 grams of an 80% solution of (2-acryloyloxy ethyl)trimethyl ammonium chloride (0.4 moles) were added to 150 grams of deionized water. To this solution were added 1.04 grams of 30% aqueous hydrogen peroxide.

Solution No. 2B was added to Solution No. 2A at 30° C. while stirring with a magnetic stir bar. A thermocouple was used to monitor the temperature and observe the reaction exotherm. The polymerization reaction began after about 2 minutes of mixing. Once the exotherm reaction was detected, water was added gradually to keep the solution viscosity suitable for stirring. A total of 250 gram of water was added over 20 minutes. A maximum polymerization temperature of 60° C. was observed about 5 minutes after the mixing of the two monomer solutions 2A and 2B. The polymer concentration was found, by evaporation of the water to be about 22%.

Quantities of superabsorbent particles were coated with Coating polymer 5, and other quantities of superabsorbent particles were coated with Coating polymer 6. For the coating of each quantity of coated superabsorbent particles, the following procedure was employed.

Each employed solution of Coating polymer was diluted to 6.67% with distilled water. 750 grams of the selected polymer solution was added to the mixing bowl of a HOBART Mixer, model N-50, available from Hobart Canada, North York, Ontario. With the solution agitated at a speed setting of "3", 500 grams of superabsorbent was added. The mixture became a fluffy mass of slightly swollen superabsorbent. The swollen superabsorbent was dried for 3 days at 80° C. and then de-agglomerated with a GRANU-GRINDER, available from C. W. Brabender, a business having offices located in Hackensack, N.J., U.S.A.

Table 4 shows CRC and TSI data of surface treated superabsorbents (e.g. SXM 9543 and SXM 9394) employing Coating Polymer 2, Coating Polymer 3 (PEO), Coating Polymer 4 (HPC), Coating Polymer 5, and Coating Polymer 6.

TABLE 4

Absorbency (CRC) and TSI of Surface Treated Superabsorbent Materials

| Superabsorbent (SAM) Composition | | | Properties of Treated SAMs | |
|---|---|---|---|---|
| SAM | Coating Polymer | Amount | CRC (g/g) | TSI (%) |
| SXM 9543 | NA | 0 | 23.0 | 0 |
| SXM 9543 | Polymer 1 | 10% | | |
| SXM 9543 | Polymer 2 | 10% | 20.4 | 1.6 |
| SXM 9543 | Polymer 3 | 5% | 22.0 | 100 |
| SXM 9543 | Polymer 4 | 5% | 22.0 | 100 |
| SXM 9394 | NA | 0 | 27.0 | 0 |
| SXM 9394 | Polymer 2 | 10% | 24.0 | 9.8 |
| SXM 9394 | Polymer 3 | 5% | 26.0 | 100 |
| SXM 9394 | Polymer 4 | 5% | 26.0 | 100 |
| SXM 9394 | Polymer 5 | 10% | 23.4 | 15.3 |
| SXM 9394 | Polymer 6 | 10% | 23.3 | 4.2 |

In Table 5, the elastomeric polymer in the meltblown fiber was VISTAMAXX 2210, which is available from ExxonMobil Chemical Company, a business having offices located Houston, Tex., U.S.A. The pulp was NB 416, which is available from Weyerhaeuser Co., a business having offices located Federal Way, Wash., U.S.A. The basis weight of the absorbent composite web was about 500 grams per square meter. The superabsorbent material in samples 19 and 21 was SXM 9394 coated by 5% PEO (Polymer 3), and the superabsorbent material in samples 23 and 25 was SXM 9543 coated by 5% PEO (Polymer 3). The samples in Table 5 were made with a Primary Air Temperature (PAT) of about 206° C.

TABLE 5

Composite Shake-Out with the SAM coated with polymer

| Sample No. | Superabsorbent (SAM) Types | Pulp wt % | VISTAMAXX 2210 wt % | SAM wt % | SAM TSI (%) | Shake-out (%) Non-cured | Shake-out (%) Heat-cured | Stretchability (%) |
|---|---|---|---|---|---|---|---|---|
| 18 | SXM 9394 | 10 | 15 | 75 | 0 | 2.60 | 2.15 | 30 |
| 19 | SXM 9394 coated by Polymer 3 | 10 | 15 | 75 | 100 | 1.15 | 0.92 | 30 |
| 20 | SXM 9394 | 0 | 17 | 83 | 0 | 2.60 | 2.35 | 50 |
| 21 | SXM 9394 coated by Polymer 3 | 0 | 17 | 83 | 100 | 1.50 | 0.81 | 50 |
| 22 | SXM 9543 | 10 | 15 | 75 | 0 | 11.10 | 8.22 | 30 |
| 23 | SXM 9543 coated by Polymer 3 | 10 | 15 | 75 | 100 | 7.76 | 3.45 | 30 |
| 24 | SXM 9543 | 0 | 17 | 83 | 0 | 18.84 | 14.50 | 50 |
| 25 | SXM 9543 coated by Polymer 3 | 0 | 17 | 83 | 100 | 6.59 | 3.03 | 50 |

Note: heat curing was conducted at 70° C. for 60 minutes.

In Table 6, the elastic polymer was VISTAMAXX 2210 polymer; the pulp was NB 416 pulp; the Elastic polymer/SAM/Pulp weight ratios were 15:75:10; the basis weight was about 500 grams per square meter. The samples in Table 6 were made with a Primary Air Temperature (PAT) about 221° C.

TABLE 6

Composite Shake-Out with the SAM coated by polymer

| Sample No. | SAM types | SAM TSI (%) | Shake-out (%) Non-cured | Shake-out (%) Heat-cured | Stretchability (%) |
|---|---|---|---|---|---|
| 25 | SXM 9394 | 0.0 | 2.02 | 1.76 | 30 |
| 26 | SXM 9394 | 9.8 | 3.85 | 3.86 | 30 |

TABLE 6-continued

Composite Shake-Out with the SAM coated by polymer

| Sample No. | SAM types | SAM TSI (%) | Shake-out (%) Non-cured | Heat-cured | Stretchability (%) |
|---|---|---|---|---|---|
| 27 | SXM 9394 coated by Polymer 2 SXM 9394 coated by Polymer 5 | 15.3 | 5.30 | 4.59 | 30 |
| 28 | SXM 9394 coated by Polymer 6 | 4.2 | 4.53 | 3.73 | 30 |

Note:
heat curing was conducted at 70° C. for 60 minutes; all samples in Table 6 contained 75 wt % SAM, 10 wt % pulp fiber and 15 wt % VISTAMAXX 2210 elastic polymer.

To provide a comparison, conventional airformed absorbent composite samples made with superabsorbent particles and woodpulp fluff can be tested with and without containment tissues. Airformed absorbent composites were made by combining superabsorbent particles and matrix fibers in an airforming system to mix and laying down a web of intermingled superabsorbent particles and matrix fibers. The web of intermingled superabsorbent particles and matrix fibers is formed directly onto a porous sheet of tissue. An example of a suitable porous tissue is designated as 9.8 pound (about 17 grams per square meter) White Forming Tissue available from American Tissue, Inc., Neenah, Wis., U.S.A. A second sheet of forming tissue was put on the top of the airformed composite. The airformed absorbent composite can then be compressed to a desired density by employing a suitable compression device, such as a Carver Press. The SAM/pulp airformed absorbent composite in samples 29 and 30 of the following Table 7 were made with 75% SXM 9394 superabsorbent material, and 25% CR 1654 woodpulp which is available from Bowater Inc. The basis weight of the airformed absorbent composite web was about 500 grams per square meter, and the samples were compressed to a density of about 0.27 g/cm³. A Shake-out test was conducted on a specimen which included a sheet of forming tissue on each side of the absorbent composite, and on a specimen of the absorbent composite which did not include the tissue sheets.

TABLE 7

SAM/Pulp Airformed Composite Shake-Out, With And Without Tissues

| Sample No. | Sample test conditions | Pulp wt % | SAM wt % | Shake-out (%) | Stretchability (%) |
|---|---|---|---|---|---|
| 29 | With tissues | 25 | 75 | 15.7 | 0 |
| 30 | Without tissues | 25 | 75 | 80.0 | 0 |

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. An article comprising, a stretchable absorbent composite including a quantity of superabsorbent particles which have a substantially continuous thermoplastic coating and are operatively contained within a matrix of elastomeric polymer fibers, wherein
said composite includes at least about 60 wt % of the superabsorbent particles and not more than about 40 wt % of the elastomeric polymer fibers, based on a total weight of the composite; wherein said thermoplastic coating includes at least one material selected from the group consisting of polyethylene oxide, polypropylene oxide, ethylene oxide-propylene oxide copolymer, polyethylene glycol, polypropylene glycol, ethylene glycol-propylene glycol copolymer, modified polysaccharides, such as hydroxypropyl cellulose, methyl cellulose, methyl ethyl cellulose, polyethylene imine, and combinations thereof; wherein said superabsorbent with said thermoplastic coating exhibits a centrifuge retention capacity of at least about 15 g/g; and wherein said thermoplastic coating has a melting-point temperature of at least 60° C. and not more than 150° C.;
said composite provides a stretchability value of at least about 30% and a shake-out value of not more than about 2%; and
the elastomeric polymer fibers have been produced from a polymer material having a melt flow rate of at least about 100 g/10 min.

2. The article as recited in claim 1, wherein said composite provides a shake-out value of not more than about 1.2%.

3. The article as recited in claim 1, wherein said composite provides a shake-out value of not more than about 0.8%.

4. The article as recited in claim 1, wherein said composite article includes at least about 5 wt % of the elastomeric polymer fibers.

5. The article as recited in claim 1, wherein said polymer fibers include an olefin elastomer material.

6. The article as recited in claim 1, wherein said polymer fibers include a surfactant.

7. The article as recited in claim 1, wherein said polymer fibers include at least about 0.1 wt % of an operative surfactant, based on a total weight of the polymer fibers and surfactant.

8. The article as recited in claim 1, wherein the composite further includes an amount of cellulosic fibers and the amount of cellulosic fibers is at least about 5 wt %, and up to about 35 wt %, based on the total weight of the composite.

9. The article as recited in claim 1, wherein said superabsorbent particles have a Thermal Stickiness Index at least about 40 and a Centrifuge Retention Capacity value at least about 20 g/g.

10. The article as recited in claim 1, wherein said superabsorbent particles have a Thermal Stickiness Index at least about 60 and a Centrifuge Retention Capacity value at least about 20 g/g.

11. The article as recited in claim 1, wherein said superabsorbent particles have a Thermal Stickiness Index at least about 80 and a Centrifuge Retention Capacity value at least about 20 g/g.

12. The article as recited in claim 1, wherein said polymer fibers have a fiber diameter which is not more than a maximum of about 20 μm and not less than a minimum of about 8 μm.

13. The article as recited in claim 1, wherein not more than about 20 wt % of said polymer fibers have a fiber diameter which is larger than about 20 μm; and not more than about 20 wt % of said polymer fibers have a fiber diameter which is less than about 8 μm.

14. The article as recited in claim 1, wherein
said composite provides a shake-out value of not more than about 1.2%; and
said polymer fibers have been produced from a quantity of polymer-melt processed at a temperature of at least about 200° C.

15. The article as recited in claim 1, wherein said superabsorbent particles have been combined with said polymer fibers during a formation of the polymer fibers, and the formation of the polymer fibers has included a meltblowing operation.

16. The article as recited in claim 1, wherein the composite article has a stretchability value of at least about 50%.

17. The article as recited in claim 1, wherein the composite article has a stretchability value of up to about 300% or more.

18. The article as recited in claim 1, further including a liquid-permeable topsheet and a backsheet; wherein the matrix of elastomeric polymer fibers and the superabsorbent particles are operatively sandwiched between the topsheet and backsheet.

19. The article as recited in claim 1, wherein
the absorbent composite includes at least about 5 wt % and not more than about 25 wt % of the elastomeric polymer fibers, and includes not more than about 15 wt % of cellulosic fibers, based on the total weight of the absorbent composite;
the absorbent composite further includes a surfactant;
the thermoplastic coating is thermally processible and water soluble;
the elastomeric polymer fibers have been produced from a quantity of polymer-melt having a temperature of at least about 200° C. and not more than about 315° C.

* * * * *